United States Patent [19]

Petrzilka et al.

[11] Patent Number: 5,238,602

[45] Date of Patent: * Aug. 24, 1993

[54] LIQUID CRYSTALS

[75] Inventors: Martin Petrzilka, Kaiseraugst; Martin Schadt, Seltisberg, both of Switzerland

[73] Assignee: Hoffmann La Roche Inc., Nutley, N.J.

[*] Notice: The portion of the term of this patent subsequent to May 7, 2008 has been disclaimed.

[21] Appl. No.: 53,778

[22] Filed: May 26, 1987

Related U.S. Application Data

[63] Continuation of Ser. No. 749,152, Jun. 26, 1985, abandoned.

[30] Foreign Application Priority Data

Jul. 16, 1984 [CH] Switzerland ............ 3457/84
May 8, 1985 [CH] Switzerland ............ 1950/85

[51] Int. Cl.$^5$ ............ C09K 19/12; C09K 19/34; C07C 69/76; C07C 69/74
[52] U.S. Cl. ............ 252/299.65; 252/299.5; 252/299.6; 252/299.61; 252/299.63; 252/299.66; 252/299.67; 252/299.68; 560/51; 560/55; 560/59; 560/61; 560/65; 560/73; 560/102; 560/106; 560/107; 560/109; 560/118; 560/126; 560/141; 560/1; 359/105; 359/106
[58] Field of Search ............ 252/299.5, 299.6, 299.61, 252/299.63, 299.65, 299.66, 299.67, 299.68; 350/350 R, 350 S; 560/51, 59, 55, 61, 73, 102, 106, 107, 109, 118, 121, 141, 1, 65; 568/329, 331, 367, 376, 642, 631, 647, 659, 661, 664; 585/20, 25; 570/128, 129; 544/215, 298, 335, 242; 549/372, 334, 369; 359/101, 105, 102, 106

[56] References Cited

U.S. PATENT DOCUMENTS

| | | |
|---|---|---|
| 3,810,879 | 5/1974 | Hay et al. |
| 3,819,531 | 6/1974 | Saeva et al. ............ 252/299.6 |
| 3,947,375 | 3/1976 | Gray et al. ............ 252/299.66 |
| 4,001,137 | 1/1977 | Steinstrasser ............ 252/299.67 |
| 4,065,489 | 12/1977 | Steinstrasser et al. ............ 252/299.65 |
| 4,147,655 | 4/1979 | Dubois et al. ............ 252/299.67 |
| 4,358,391 | 11/1982 | Finkelman et al. ............ 252/299.67 |
| 4,363,767 | 12/1982 | Demus et al. ............ 252/299.63 |

(List continued on next page.)

FOREIGN PATENT DOCUMENTS

| | | | |
|---|---|---|---|
| 122389 | 10/1984 | European Pat. Off. | ....... 256/299.13 |
| 2944591 | 5/1981 | Fed. Rep. of Germany. | |
| 3331515 | 3/1985 | Fed. Rep. of Germany | ....... 252/299.63 |
| 2377441 | 8/1978 | France. | |
| 57-67538 | 4/1982 | Japan | ....... 252/299.63 |
| 59-199649 | 11/1984 | Japan | ....... 252/299.66 |
| 60-112723 | 6/1985 | Japan. | |
| 60112723 | 6/1985 | Japan | ....... 252/299.63 |
| 61-27928 | 2/1986 | Japan | ....... 252/299.63 |
| 61-27929 | 2/1986 | Japan | ....... 252/299.63 |
| 61-27931 | 2/1986 | Japan | ....... 252/299.66 |
| 1432692 | 4/1976 | United Kingdom | ....... 252/299.64 |

OTHER PUBLICATIONS

Hsu, E. C., et al., Mol. Cryst. Liq. Cryst., vol. 33, pp. 35–45 (1976).

(Continued on next page.)

Primary Examiner—Philip C. Tucker
Attorney, Agent, or Firm—George M. Gould; George W. Johnston

[57] ABSTRACT

Compounds of the formula

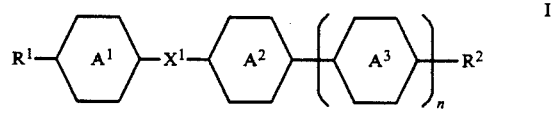

wherein n stands for the number 0 or 1; the rings $A^1$, $A^2$ and $A^3$ represent 1,4-phenylene, 2-fluoro-1,4-phenylene or trans-1,4-cyclohexylene or one of these rings also represents a 2,5-disubstituted pyrimidine ring or a trans-2,5-disubstituted m-dioxane ring; $X^1$ represents a single covalent bond, —COO—, —OOC—, —CH$_2$CH$_2$—, p—C$_6$H$_4$—, —CH$_2$CH$_2$—p— C$_6$H$_4$—, —CH$_2$CH$_2$—p—C$_6$H$_4$—CH$_2$CH$_2$— or, insofar as the rings $A^1$ and $A^2$ represent 1,4-phenylene, also —NON—; $R^2$ represents 1E-alkenyl, 2Z-alkenyl, 3E-alkenyl, 4-alkenyl or alkenyloxy, with the proviso that the oxygen atom in alkenyloxy is linked with a saturated carbon atom; and $R^1$ signifies 1E-alkenyl, 2Z-alkenyl, 3E-alkenyl, 4-alkenyl or, insofar as $R^2$ represents alkenyloxy, also alkyl, their manufacture, as well as liquid crystalline mixtures and the use for electro-optical purposes.

14 Claims, No Drawings

U.S. PATENT DOCUMENTS

| | | | |
|---|---|---|---|
| 4,388,453 | 6/1983 | Finkelmann et al. | 252/299.67 |
| 4,410,570 | 10/1983 | Kreuzer et al. | 252/299.01 |
| 4,528,114 | 7/1985 | Petrzilka | 252/299.63 |
| 4,565,425 | 1/1986 | Petrzilka et al. | 252/299.61 |
| 4,621,901 | 11/1986 | Petrzilka et al. | 252/299.63 |
| 4,629,581 | 12/1986 | Boller et al. | 252/299.63 |
| 4,654,421 | 3/1987 | Tanaka et al. | 252/299.61 |
| 4,676,604 | 6/1987 | Petrzilka | 252/299.61 |
| 4,707,295 | 11/1987 | Pohl et al. | 252/299.63 |
| 4,709,030 | 11/1987 | Petazilka et al. | 252/299.61 |
| 4,710,015 | 12/1987 | Schad et al. | 252/299.63 |
| 4,719,032 | 1/1988 | Wachtler et al. | 252/299.63 |
| 4,726,911 | 2/1988 | Krause et al. | 252/299.61 |
| 5,013,477 | 5/1991 | Buchecker et al. | 252/299.63 |

OTHER PUBLICATIONS

Goodby, J. W., et al., Liq. Cryst. Ordered Fluids, vol. 4, pp. 89–110 (1989).
Finkelmann, H., Phil. Trans. R. Soc. Lond. A, vol. 309, pp. 105–114 (1983).
Dabrowski, R., et al., Mol. Cryst. Liq. Cryst., vol. 87, pp. 109–135 (1982).
Kamogawa, H., et al., Bull. Chem. Soc. Jpn, vol. 56, pp. 3517–3518 (1983).
Tanigaki, Patent Abstracts of Japan vol. 9, No. 66 (C-271) (1789) Mar. (1985).
Masada, patent Abstracts of Japan vol. 6, No. 143 (C-117) (1021) (Aug. 1982).
Petrzilka, Mol. Cryst. Liq. Cryst. vol. 111, (1984) pp. 329–346.
Derwent Abstract E14LOG (1983).
Dubois, Nouveau Journal de Chimie 2 643 (1978).
Mizuno, Mol. Cryst. Liq. Cryst. 41 (letters) pp. 161–166 (1978).
Kamogawa, Bull. Chem. Soc. Japan 52 3125–3126 (1979).
Dabrowski, Mol. Liq. Cryst. (1982) vol. 87 pp. 109–135.
Ringsdorf, Macromol Chem. Rapid Commun. p. 3,557–562, (1982).
Goodby, Liq. Cryst. Ordered Fluids 4 89–MO. (1984).
Stevens, Macromolecules 17 (1984) pp. 851–856.
Jones, J. Org. Chem. 49 (1984) 4947–4951.
Gershuni, J. Chem. Soc. Chem. Commun. 84 517–520 (1980).
Merck, Chemical Abstracts 69 4362IV (1968).
Tanigaki, Chemical Abstracts 102:78559h (1985).
Finkelmann, Mol. Cryst. Liq. Cryst (1982) 89 pp. 23–36 (1982).
Holdaway, Chemical Abstracts 89:129982p (1952).
Mitin, Chemical Abstracts 61: 1951a (1978).
Fontanille, Chemical Abstracts 91:141450 (1979).
Hixson, J. Chem. Soc. Chem. Commun. pp. 65–66 (1984).
Nishimura, et al. Polymer Journal vol. 13 No. 7 pp. 635–639 (1981).
Tanimoto, et al. Synthetic Comm. 4, 193 (1974).
Toyonaka, Polymer Journal 13, 635 (1981).
Carpino, et al. J. Org. Chem. 48, 661 (1983).

LIQUID CRYSTALS

This application is a continuation of application Ser. No. 749,152, filed Jun. 26, 1985 now abandoned.

BACKGROUND OF THE INVENTION

1. Field of the Invention

The present invention is concerned with novel compounds having alkenyl or alkenyloxy groups, their manufacture, liquid crystalline mixtures which contain these compounds as well as the use of these compounds and mixtures for electro-optical purposes.

2. Description

Liquid crystals have recently gained considerable importance as dielectrics in indicating devices, since the optical properties of such substances can be influenced by an applied voltage. Electro-optical devices based on liquid crystals are well known to the person skilled in the art and can be based on various effects such as, for example, the dynamic scattering, the deformation of aligned phases (DAP cell) the Schadt-Helfrich effect (twisted-nematic cell), the guest/host effect (guest/host cell) or a cholesteric-nematic phase transition (phase change cell).

The liquid crystals which are used must have a good stability towards heat, moisture, air, electromagnetic radiation, electrical fields and the like. Further, they should be colourless, should have short response times and low viscosity, should give a good contrast and should have a nematic or cholesteric mesophase in the entire temperature range in which the liquid crystal cell is to be operated. Since liquid crystals are usually used as mixtures, it is, moreover, important that the components have a good miscibility with one another and at the same time form a nematic or cholesteric mesophase. Other properties such as, for example, the electrical conductivity, the threshold potential, the multiplexibility and the dielectric anisotropy must fulfil different conditions depending on the type of cell which is used.

SUMMARY OF THE INVENTION

The present invention concerns compounds of the formula

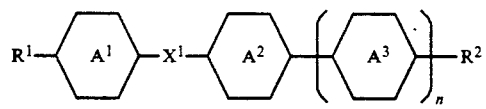

wherein n stands for the number 0 or 1; the rings $A^1$, $A^2$ and $A^3$ represent 1,4-phenylene, 2-fluoro-1,4-phenylene or trans-1,4-cyclohexylene or one of these rings also represents a 2,5-disubstituted pyrimidine ring or a trans-2,5-disubstituted m-dioxane ring; $X^1$ represents a single covalent bond, —COO—, —OOC—, —CH$_2$CH$_2$—, p—C$_6$H$_4$—, —CH$_2$CH$_2$—p— C$_6$H$_4$—, —CH$_2$CH$_2$—p—C$_6$H$_4$—CH$_2$CH$_2$— or, insofar as the rings $A^1$ and $A^2$ represent 1,4-phenylene, also —NON—; $R^2$ represents 1E-alkenyl, 2Z-alkenyl, 3E-alkenyl, 4-alkenyl, or alkenyloxy, with the proviso that the oxygen atom in alkenyloxy is linked with a saturated carbon atom; and $R^1$ signifies 1E-alkenyl, 2Z-alkenyl, 3E-alkenyl, 4-alkenyl or, insofar as $R^2$ represents alkenyloxy, also alkyl.

The compounds in accordance with the invention have the required properties mentioned above and, moreover, exhibit with respect to various parameters improved values compared with known liquid crystal components.

DETAILED DESCRIPTION OF THE INVENTION

The present invention is directed to a compound of the formula

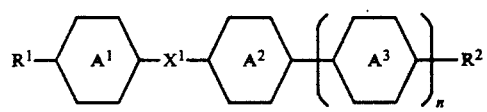

wherein n is the integer number 0 or 1; the rings $A^1$, $A^2$ and $A^3$ independently are 1,4-phenylene, 2-fluoro-1,4-phenylene or trans-1,4-cyclohexylene or one of these rings also is 2,5-disubstituted pyrimidine or trans-2,5-disubstituted m-dioxane; $X^1$ is a single covalent bond, —COO—, —OOC—, —CH$_2$CH$_2$—, p—C$_6$H$_4$—, —CH$_2$CH$_2$—p—C$_6$H$_4$—, —CH$_2$CH$_2$—p—C$_6$H$_4$—CH$_2$CH$_2$— or, when rings $A^1$ and $A^2$ are 1,4-phenylene, $X^1$ also can be —NON—; $R^2$ is 1E-alkenyl, 2Z-alkenyl, 3E-alkenyl, 4-alkenyl or alkenyloxy, with the proviso that the oxygen atom in alkenyloxy is linked with a saturated carbon atom; and $R^1$ is 1E-alkenyl, 2Z-alkenyl, 3E-alkenyl, 4-alkenyl or, when $R^2$ is alkenyloxy, $R^1$ also can be alkyl.

The compounds in accordance with the invention have the required properties mentioned above and, moreover, exhibit with respect to various parameters improved values compared with known liquid crystal components. For example, the compounds with side-chains such as 1E-alkenyl, 3E-alkenyl, (2E-alkenyl)oxy, (4-alkenyl)oxy etc. have, in general, improved mesophase ranges and clearing points and mostly also shorter response times in comparison to the corresponding compounds with saturated side-chains. On the other hand, the compounds with side-chains such as 2Z-alkenyl, 4-alkenyl, (3-alkenyl)oxy, (5-alkenyl)oxy etc give, in general, a low viscosity (especially an improved rotation viscosity $\gamma_1$), low threshold potentials, a favourable ratio of the elastic constants $k_{33}$ (bend) and $k_{11}$ (splay) and therefore steep transmission curves and a good multiplexibility.

The compounds of formula I have a relatively small absolute value of the dielectric anisotropy ($\Delta\epsilon=\epsilon_{\parallel} - \epsilon_{\perp}$, $\epsilon_{\parallel}$ signifying the dielectric constant along the longitudinal axis of the molecule and $\epsilon_{\perp}$ signifying the dielectric constant perpendicular thereto) and a low conductivity. They are therefore suitable for any mixtures, i.e. for mixtures with positive, negative or small absolute dielectric anisotropy, and for all usual liquid crystal cells, especially for twisted-nematic cells and guest/host cells.

In the scope of the present invention the term "1E-alkenyl" embraces unsaturated, univalent aliphatic residues of 2 to 12 carbon atoms such as vinyl, 1E-propenyl, 1E-butenyl, 1E-pentenyl, 1E-hexenyl, 1E-heptenyl, 1E-octenyl, 1E-nonenyl and 1E-decenyl. The term "2Z-alkenyl" embraces unsaturated, univalent aliphatic residues of 3 to 12 carbon atoms such as allyl, 2Z-butenyl, 2Z-pentenyl, 2Z-hexenyl, 2Z-heptenyl, 2Z-octenyl, 2Z-nonenyl and 2Z-decenyl. The term "3E-alkenyl" embraces unsaturated, univalent aliphatic residues of 4 to 12 carbon atoms such as 3-butenyl, 3E-pentenyl, 3E-hexenyl, 3E-heptenyl, 3E-octenyl, 3E-nonenyl and 3E-decenyl. The term "4-alkenyl" embraces unsaturated, univalent aliphatic residues of 5 to 12 carbon atoms such as 4-pentenyl and the E- and/or Z-form of 4-hexenyl, 4-heptenyl, 4-octenyl, 4-nonenyl and 4-decenyl.

The term "alkenyloxy" in $R^2$ denotes alkenyloxy groups in which the oxygen atom is linked directly with a saturated carbon atom (i.e. groups which have one or more carbon atoms between the double bond and the oxygen atom), such as (2E-alkenyl)oxy, (3-alkenyl)oxy, (4-alkenyl)oxy, (5-alkenyl)oxy and the like. The term "(2E-alkenyl)oxy" embraces alkenyloxy residues such as allyloxy, (2E-butenyl)oxy, (2E-pentenyl)oxy, (2E-hexenyl)oxy, (2E-heptenyl)oxy, (2E-octenyl)oxy, (2E-nonenyl)oxy and (2E-decenyl)oxy. The term "(3-alkenyl)oxy" embraces alkenyloxy residues such as (3-butenyl)oxy and the E- and/or Z-form of (3-pentenyl)oxy, (3-hexenyl)oxy, (3-heptenyl)oxy, (3-octenyl)oxy, (3-nonenyl)oxy and (3-decenyl)oxy. The term "(4-alkenyl)oxy" embraces alkenyloxy residues such as (4-pentenyl)oxy and the E- and/or Z-form of (4-hexenyl)oxy, (4-heptenyl)oxy, (4-octenyl)oxy, (4-nonenyl)oxy and (4-decenyl)oxy. The term "(5-alkenyl)oxy" embraces alkenyloxy residues such as (5-hexenyl)oxy and the E- and/or Z-form of (5-heptenyl)oxy, (5-octenyl)oxy, (5-nonenyl)oxy and (5-decenyl)oxy.

The term "alkyl" signifies in the scope of the present invention straight-chain or branched alkyl residues of 1 to 12 carbon atoms such as methyl, ethyl, propyl, isopropyl, butyl, 2-methylbutyl, pentyl, hexyl, heptyl, octyl, nonyl and decyl. The above designation p—$C_6H_4$— stands for 1,4-phenylene and the designation —NON— stands for an azoxy group —N=N(O)— or —N(O)=N—. The term "halogen" denotes in the scope of the present invention chlorine, bromine or iodine. The term "alkali metal" embraces lithium, sodium and potassium.

Formula I above embraces in particular the following sub-formulae:

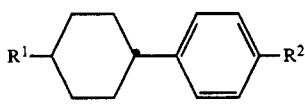
Ia

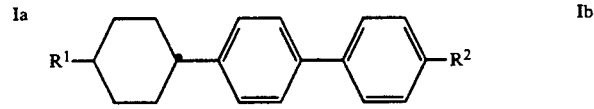
Ib

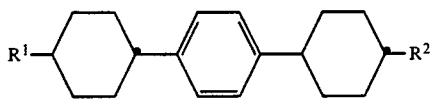
Ic

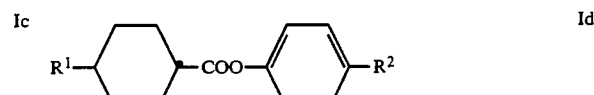
Id

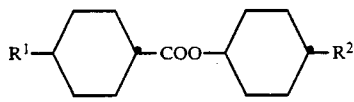
Ie

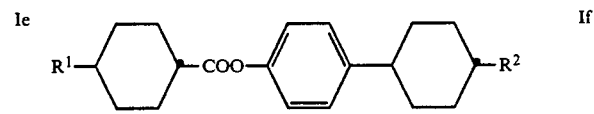
If

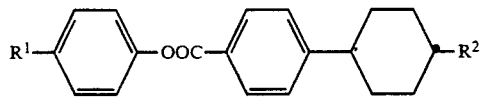
Ig

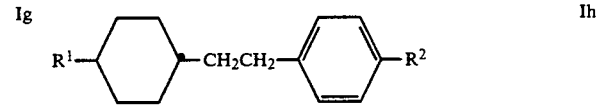
Ih

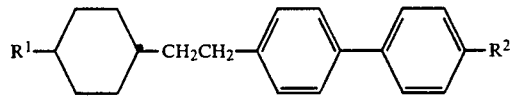
Ii

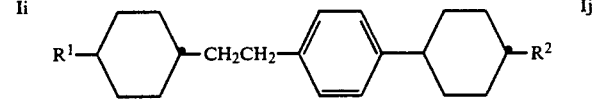
Ij

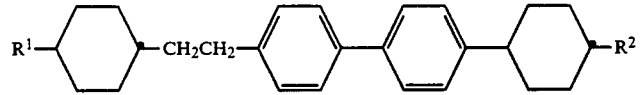
Ik

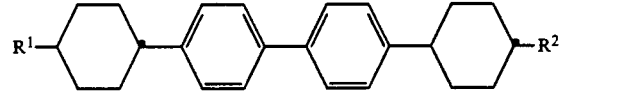
Il

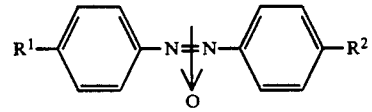

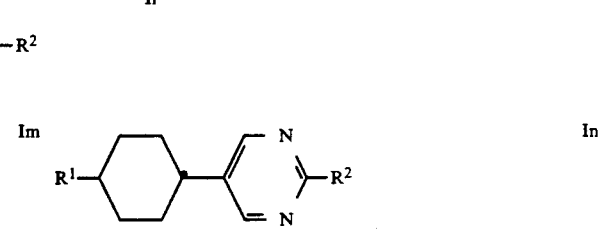
Im In

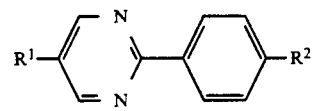
Io

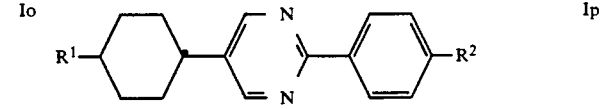
Ip

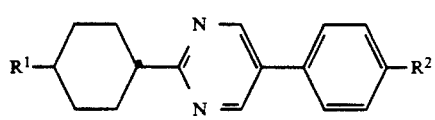

-continued

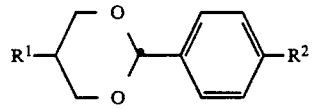

wherein $R^1$ and $R^2$ have the above significances.

$R^1$ and $R^2$ preferably stand for straight-chain residues with a maximum of 12 carbon atoms, i.e. for straight-chain 1E-alkenyl with 2 to 12 carbon atoms, straight-chain 2Z-alkenyl with 3 to 12 carbon atoms, straight-chain 3E-alkenyl with 4 to 12 carbon atoms, straight-chain 4-alkenyl with 5 to 12 carbon atoms, straight-chain alkyl with 1 to 12 carbon atoms or straight-chain alkenyloxy with a maximum of 12 carbon atoms, such as straight-chain (2E-alkenyl)oxy with 3 to 12 carbon atoms, straight-chain (3-alkenyl)oxy with 4 to 12 carbon atoms, straight-chain (4-alkenyl)oxy with 5 to 12 carbon atoms, straight-chain (5-alkenyl)oxy with 6 to 12 carbon atoms and the like. Residues $R^1$ and $R^2$ with a maximum of 7 carbon atoms are especially preferred.

Preferred alkenyloxy residues $R^2$ are (5-alkenyl)oxy, (4-alkenyl)oxy and especially (3-alkenyl)oxy and (2E-alkenyl)oxy. Preferred alkenyl residues $R^1$ and $R^2$ are 1E-alkenyl, 3E-alkenyl and 4-alkenyl. When $R^2$ stands for alkenyloxy, $R^1$ can preferably also signify alkyl. Especially preferred compounds of formula I are those in which $R^2$ signifies (2E-alkenyl)oxy or at least one of the residues $R^1$ and $R^2$ signifies 1E-alkenyl or 3E-alkenyl. Preferably, 4-alkenyl stands for 4Z-alkenyl, (3-alkenyl)oxy stands for (3Z-alkenyl)oxy, (4-alkenyl)oxy stands for (4E-alkenyl)oxy and (5-alkenyl)oxy stands for (5Z-alkenyl)oxy.

Residues $R^1$ and $R^2$ which are attached to an aromatic ring, i.e. to a benzene or pyrimidine ring, preferably signify 3E-alkenyl, 4-alkenyl or in the case of $R^2$ also alkenyloxy or in the case of $R^1$ also alkyl.

Lateral fluorine substituents mainly give improved nematic tendencies. In general, however, compounds without lateral fluorine substituents (i.e. without a 2-fluoro-1,4-phenylene group) are preferred. $X^1$ preferably denotes a single covalent bond, —COO—, —OOC—, —CH$_2$CH$_2$— or p—C$_6$H$_4$—. Preferably, n denotes the number 0.

Ring $A^1$ preferably stands for 1,4-phenylene when $X^1$ denotes —OOC—, -N=N(O)- or -N(O)=N- and preferably for trans-1,4-cyclohexylene in the remaining cases. If $X^1$ denotes a single covalent bond, ring $A^1$ can preferably also stand for a 2,5-disubstituted pyrimidine ring or a trans-2,5-disubstituted m-dioxane ring; in this case ring $A^2$ denotes trans-1,4-cyclohexylene or preferably 1,4-phenylene. Ring $A^3$ preferably stands for 1,4-phenylene or trans-1,4-cyclohexylene. Ring $A^2$ preferably stands for 1,4-phenylene, a 2,5-disubstituted pyrimidine ring or, when n signifies the number 0, also for trans-1,4-cyclohexylene.

An especially preferred group of compounds of formula I comprises those in which n stands for the number 0, ring $A^1$ represents trans-1,4-cyclohexylene, ring $A^2$ represents 1,4-phenylene and $X^1$ denotes a single covalent bond, —COO—, —CH$_2$CH$_2$— or p—C$_6$H$_4$—.

Examples of preferred compounds in accordance with the invention are the compounds of formulae Ia, Ib, Ic, Id, Ie, If, Ig, Ih, Ii, Ij, Ik, Il, Im, In, Io, Ip, Iq and Ir in which $R^1$ and $R^2$ in each case have the following significances:

| $R^1$ | $R^2$ |
| --- | --- |
| Propyl | Allyloxy |
| Propyl | (2E-Butenyl)oxy |
| Propyl | (3-Butenyl)oxy |
| Pentyl | Allyloxy |
| Pentyl | (2E-Butenyl)oxy |
| Pentyl | (3-Butenyl)oxy |
| 1E-Propenyl | 1E-Propenyl |
| 1E-Propenyl | 1E-Butenyl |
| 1E-Propenyl | 1E-Pentenyl |
| 1E-Propenyl | 3-Butenyl |
| 1E-Propenyl | 3E-Pentenyl |
| 1E-Propenyl | 4-Pentenyl |
| 1E-Propenyl | 4Z-Hexenyl |
| 1E-Propenyl | Allyloxy |
| 1E-Propenyl | (2E-Butenyl)oxy |
| 1E-Propenyl | (3-Butenyl)oxy |
| 1E-Butenyl | 1E-Propenyl |
| 1E-Butenyl | 1E-Butenyl |
| 1E-Butenyl | 1E-Pentenyl |
| 1E-Butenyl | 3-Butenyl |
| 1E-Butenyl | 3E-Pentenyl |
| 1E-Butenyl | 4-Pentenyl |
| 1E-Butenyl | 4Z-Hexenyl |
| 1E-Butenyl | Allyloxy |
| 1E-Butenyl | (2E-Butenyl)oxy |
| 1E-Butenyl | (3-Butenyl)oxy |
| 1E-Pentenyl | 1E-Propenyl |
| 1E-Pentenyl | 1E-Butenyl |
| 1E-Pentenyl | 1E-Pentenyl |
| 1E-Pentenyl | 3-Butenyl |
| 1E-Pentenyl | 3E-Pentenyl |
| 1E-Pentenyl | 4-Pentenyl |
| 1E-Pentenyl | Allyloxy |
| 1E-Pentenyl | (2E-Butenyl)oxy |
| 1E-Pentenyl | (3-Butenyl)oxy |
| 3-Butenyl | 1E-Propenyl |
| 3-Butenyl | 1E-Butenyl |
| 3-Butenyl | 1E-Pentenyl |
| 3-Butenyl | 3-Butenyl |
| 3-Butenyl | 3E-Pentenyl |
| 3-Butenyl | 3E-Hexenyl |
| 3-Butenyl | 4-Pentenyl |
| 3-Butenyl | Allyloxy |
| 3-Butenyl | (2E-Butenyl)oxy |
| 3-Butenyl | (3-Butenyl)oxy |
| 3-Butenyl | (3Z-Pentenyl)oxy |
| 3E-Pentenyl | 1E-Propenyl |
| 3E-Pentenyl | 1E-Butenyl |
| 3E-Pentenyl | 1E-Pentenyl |
| 3E-Pentenyl | 3-Butenyl |
| 3E-Pentenyl | 3E-Pentenyl |
| 3E-Pentenyl | 4-Pentenyl |
| 3E-Pentenyl | Allyloxy |
| 3E-Pentenyl | (2E-Butenyl)oxy |
| 3E-Pentenyl | (3-Butenyl)oxy |
| 3E-Hexenyl | 1E-Propenyl |
| 3E-Hexenyl | 1E-Butenyl |
| 3E-Hexenyl | 3-Butenyl |
| 3E-Hexenyl | 4-Pentenyl |
| 3E-Hexenyl | Allyloxy |
| 3E-Hexenyl | (2E-Butenyl)oxy |
| 3E-Hexenyl | (3-Butenyl)oxy |
| 3E-Heptenyl | 1E-Propenyl |
| 3E-Heptenyl | 1E-Butenyl |
| 3E-Heptenyl | 3-Butenyl |
| 3E-Heptenyl | 4-Pentenyl |
| 3E-Heptenyl | Allyloxy |
| 3E-Heptenyl | (2E-Butenyl)oxy |
| 3E-Heptenyl | (3-Butenyl)oxy |
| 4-Pentenyl | 1E-Propenyl |
| 4-Pentenyl | 1E-Butenyl |
| 4-Pentenyl | 1E-Pentenyl |
| 4-Pentenyl | 3-Butenyl |

-continued

| R¹ | R² |
| --- | --- |
| 4-Pentenyl | 3E-Pentenyl |
| 4-Pentenyl | Allyloxy |
| 4-Pentenyl | (2E-Butenyl)oxy |
| 4Z-Hexenyl | 1E-Propenyl |
| 4Z-Hexenyl | 1E-Butenyl |
| 4Z-Hexenyl | 3-Butenyl |
| 4Z-Hexenyl | Allyloxy | as well as the compounds of formula I named in the chemical Examples hereinafter.

The compounds of formula I can be manufactured in accordance with the invention by the following process:

a) for the manufacture of the compounds of formula I in which $X^1$ denotes —COO— or —OOC—, esterifying a compound of the formula

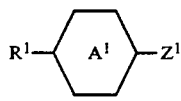

II or a reactive derivative thereof with a compound of the formula

III wherein one of the groups $Z^1$ and $Z^2$ represents —COOH and the other represents —OH; and $R^1$, $R^2$, n and the rings $A^1$, $A^2$ and $A^3$ have the above significance, or a reactive derivative thereof, or b) for the manufacture of the compounds of formula I in which one of the rings $A^1$, $A^2$ and $A^3$ represents a trans-2,5-disubstituted m-dioxane ring and $X^1$ denotes a single covalent bond, —CH₂CH₂—, p—C₆H₄—, —CH₂CH₂—p—C₆H₄— or —CH₂CH₂—p—C₆H₄—CH₂CH₂—, reacting a compound of the formula

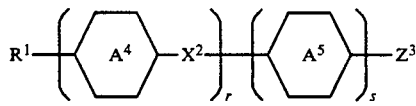

IV with a compound of the formula

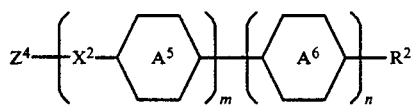

V wherein one of the groups $Z^3$ and $Z^4$ denotes —CH(CH₂OH)₂ and the other represents —CHO; $X^2$ denotes a single covalent bond, —CH₂CH₂—, p—C₆H₄—, —CH₂CH₂—p—C₆H₄— or —CH₂CH₂—p—C₆H₄—CH₂CH₂—; the rings $A^4$, $A^5$ and $A^6$ represent 1,4-phenylene, 2-fluoro-1,4-phenylene or trans-1,4-cyclohexylene; m, n, r and s signify the numbers 0 or 1 and the sum (m+n+r+s) of these indices is 1 or 2, whereby s can only signify the number 1 when r stands for the number 1 and m can only signify the number 1 when r stands for the number 0; and $R^1$ and $R^2$ have the above significances, or c) for the manufacture of the compounds of formula I in which one of the rings $A^1$, $A^2$ and $A^3$ represents a 2,5-disubstituted pyrimidine ring and $X^1$ denotes a single covalent bond, —CH₂CH₂—, p—C₆H₄—, —CH₂CH₂—p—C₆H₄— or —CH₂CH₂—p—C₆H₄—CH₂CH₂—, reacting a compound of formula IV with a compound of formula V in which one of the groups $Z^3$ and $Z^4$ represents H₂N—C=NH.HCl and the other represents OHC—C=CHOR³, $R^3$ denotes alkyl and $X^2$, $R^1$, $R^2$, m, n, r, s and the rings $A^4$, $A^5$ and $A^6$ have the above significances, in the presence of a base, or d) for the manufacture of the compounds of formula I in which $R^1$ signifies an alkenyl group and $R^2$ signifies an alkenyl group or an alkenyloxy group and $X^1$ denotes a single covalent bond —CH₂CH₂—, p—C₆H₄—, —CH₂CH₂—p—C₆H₄— or —CH₂CH₂—p—C₆H₄—CH₂CH₂—, reacting a compound of the formula

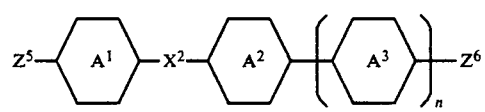

VI wherein $Z^5$ represents OHC(CH₂)$_p$ and $Z^6$ represents 1E-alkenyl, 2Z-alkenyl, 3E-alkenyl, 4-alkenyl or alkenyloxy, or $Z^5$ represents 1E-alkenyl, 2Z-alkenyl, 3E-alkenyl or 4-alkenyl and $Z^6$ represents (CH₂)$_q$CHO, or $Z^5$ represents OHC(CH₂)$_p$ and $Z^6$ represents (CH₂)$_q$CHO; p and q stand for the numbers 0, 1, 2 or 3; $X^2$ denotes a single covalent bond, —CH₂CH₂—, p—C₆H₄—, —CH₂CH₂—p—C₆H₄— or —CH₂CH₂—p—C₆H₄—CH₂CH₂—; and n and the rings $A^1$, $A^2$ and $A^3$ have the above significances, with an alkyltriphenylphosphonium halide in the presence of a base, or e) for the manufacture of the compounds of formula I in which $R^2$ represents alkenyloxy, etherifying a compound of the formula

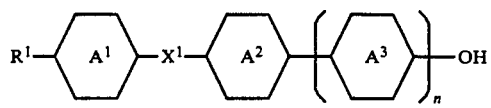

VII wherein $R^1$ signifies 1E-alkenyl, 2Z-alkenyl, 3E-alkenyl, 4-alkenyl or alkyl and $X^1$, n and the rings $A^1$, $A^2$ and $A^3$ have the above significances, with a compound of the formula

VIII wherein k stands for a whole number and is at least 1, R denotes hydrogen or alkyl and $Z^7$ signifies halogen, or f) for the manufacture of the compounds of formula I in which $X^1$ denotes -NON-, reacting a compound of the formula

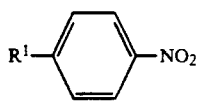

with a compound of the formula

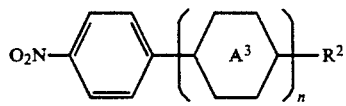

wherein $R^1$, $R^2$, n and the ring $A^3$ have the above significances,
in the presence of a reducing agent, or g) for the manufacture of the compounds of formula I in which one of the residues $R^1$ and $R^2$ signifies 3E-alkenyl or 4-alkenyl and the other signifies 1E-alkenyl, 2Z-alkenyl, 3E-alkenyl or 4-alkenyl, the rings $A^1$, $A^2$ and $A^3$ represent 1,4-phenylene, 2-fluoro-1,4-phenylene or trans-1,4-cyclohexylene and $X^1$ denotes a single covalent bond, —CH$_2$CH$_2$—, p—C$_6$H$_4$—, —CH$_2$CH$_2$—p—C$_6$H$_4$— or —CH$_2$CH$_2$—p—C$_6$H$_4$—CH$_2$CH$_2$—, reducing a compound of the formula

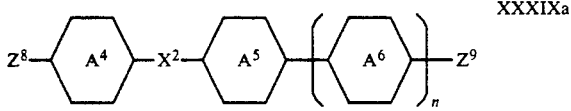

wherein n stands for the number 0 or 1; the rings $A^4$, $A^5$ and $A^6$ represent 1,4-phenylene, 2-fluoro-1,4-phenylene or trans-1,4-cyclohexylene; $X^2$ denotes a single covalent bond, —CH$_2$CH$_2$—, p—C$_6$H$_4$—, —CH$_2$CH$_2$—p—C$_6$H$_4$— or —CH$_2$CH$_2$—p—C$_6$H$_4$—CH$_2$CH$_2$—; and one of the residues $Z^8$ and $Z^9$ signifies 3E-alkenoyl or 4-alkenoyl and the other signifies 1E-alkenyl, 2Z-alkenyl, 3E-alkenyl, 4-alkenyl, 3E-alkenoyl or 4-alkenoyl, or h) for the manufacture of the compounds of formula I in which one of the residues $R^1$ and $R^2$ signifies 3E-alkenyl or 4-alkenyl and the other signifies 1E-alkenyl, 2Z-alkenyl, 3E-alkenyl or 4-alkenyl and $X^1$ denotes a single covalent bond, —CH$_2$CH$_2$—, p—C$_6$H$_4$—, —CH$_2$CH$_2$—p—C$_6$H$_4$— or —CH$_2$CH$_2$—p—C$_6$H$_4$—CH$_2$CH$_2$—, reacting a compound of the formula

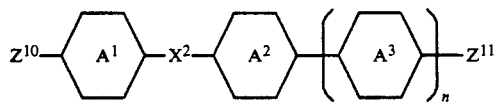

wherein one of the residues $Z^{10}$ and $Z^{11}$ signifies halomethyl and the other signifies 1E-alkenyl, 2Z-alkenyl, 3E-alkenyl, 4-alkenyl or halomethyl; $X^2$ denotes a single covalent bond, —CH$_2$CH$_2$—, p—C$_6$H$_4$—, —CH$_2$CH$_2$—p—C$_6$H$_4$— or —CH$_2$CH$_2$—p—C$_6$H$_4$—CH$_2$CH$_2$—; and n and the rings $A^1$, $A^2$ and $A^3$ have the above significances, with a (2E-alkenyl)magnesium halide or a (3-alkenyl)magnesium halide in the presence of copper(I) iodide.

The esterification of the compounds of formulae II and III or of reactive derivatives thereof (e.g. acid chloride, alkali metal alcoholate or alkali metal phenolate) in accordance with process variant a) can be carried out in a manner known per se. The esterification of the acid chlorides can be carried out, for example, in diethyl ether, tetrahydrofuran, dimethylformamide, benzene, toluene, carbon tetrachloride, pyridine and the like. The esterification of a compound of formula II with a compound of formula III is preferably carried out in the presence of 4-(dimethylamino)pyridine and dicyclohexylcarbodiimide or in the presence of oxalyl chloride and dimethylformamide. The temperature and pressure at which these esterification reactions are carried out are not critical. In general, these reactions are carried out at atmospheric pressure and a temperature between about −30° C. and the boiling temperature of the reaction mixture.

The reaction of a compound of formula IV with a compound of formula V in accordance with process variant b) can be carried out in a manner known per se. In place of the aldehyde there can also be used a suitable acetal, e.g. the dimethyl acetal. The reaction is conveniently carried out in an inert organic solvent (for example, an aromatic hydrocarbon such as benzene, toluene or xylene) in the presence of a catalytic amount of an organic or inorganic acid such as p-toluenesulphonic acid or dry hydrogen chloride. The temperature and pressure are not critical, but the reaction is preferably carried out at reflux temperature and atmospheric pressure.

The reaction of a compound of formula IV with a compound of formula V in accordance with process variant c) can also be carried out in a manner known per se. The reaction is conveniently carried out in water or an organic solvent (preferably an alcohol such as methanol, ethanol, ethylene glycol and the like) in the presence of a base, preferably an alkali metal alcoholate such as sodium methylate or sodium ethylate. $R^3$ conveniently embraces alkyl residues with 1 to 5 carbon atoms such as methyl, ethyl, propyl, isopropyl and the like. The temperature and pressure at which this reaction is carried out are not critical. However, in general, the reaction is carried out at atmospheric pressure and a temperature between room temperature and the reflux temperature.

The reaction of a compound of formula VI with an alkyl-triphenylphosphonium halide (preferably an alkyl-triphenylphosphonium bromide) in the presence of a base (in accordance with process variant d) can be carried out in a manner known per se. Suitable bases are potassium t-butylate, sodium methylate, potassium carbonate, sodium hydride, sodium amide and the like. The reaction is conveniently carried out in an inert organic solvent, for example an ether such as diethyl ether, tetrahydrofuran or dioxan. The temperature and pressure are not critical; in general, however, the reaction is carried out at atmospheric pressure and a temperature of room temperature up to the reflux temperature.

The etherification of a compound of formula VII with a compound of formula VIII (in accordance with process variant e) can be carried out in a manner known per se. The reaction is conveniently carried out in the presence of a base (for example, an alkali metal, an alkali metal hydride or an alkali metal carbonate such as sodium, sodium hydride, potassium hydride or potassium carbonate) in an inert organic solvent, for example a hydrocarbon, an ether, a ketone or an amide such as benzene, tetrahydrofuran, acetone or dimethylformamide. Preferably, $Z^7$ stands for bromine or iodine. The compounds of formula VII in which the hydroxy group is attached to a saturated ring (cyclohexane, m-dioxane) are preferably reacted in the presence of sodium hydride or potassium hydroxide in a tetrahydrofuran/dimethylformamide mixture at about 0° C. to room temperature. The compounds of formula VII in which the hydroxy group is attached to an aromatic ring (benzene, pyrimidine) are preferably etherified in the presence of an alkali metal carbonate in acetone at a temperature of room temperature to the reflux temperature, preferably at reflux temperature. The temperature and pressure at which these etherification reactions are carried out are, however, not critical and, in general, the reactions can be carried out at atmospheric pressure and a temperature of about 0° C. to the reflux temperature.

The reaction of a compound of formula IX with a compound of formula X in accordance with process variant f) can be carried out in a manner known per se. As the reducing agents there are suitable the usual reducing agents which are suitable for the reduction of nitro compounds to nitroso compounds and hydroxylamines, such as glucose, alcohols (e.g. methanol, ethanol), aldehydes (e.g. formaldehyde), hydrazine, magnesium, zinc, tin(II) compounds and the like. The reaction can be carried out under the usual conditions which are described in the literature [e.g. K. H. Schündehütte in Houben-Weyl: Methoden der organischen Chemie volume X-3, page 745 et seq, (1965), Georg Thieme Verlag, Stuttgart]. When $R^1$ and $R^2$ in formulae IX and X have different significances or when n stands for the number 1, there are generally obtained in this reaction statistical mixtures of several azoxy compounds. These mixtures can be used as such or, if desired, can be separated in a manner known per se, e.g. by chromatography.

The reduction of a compound of formula XXXIXa in accordance with process variant g) can be carried out in a manner known per se. For example, a compound of formula XXXIXa can be reacted with hydrazine in the presence of a base (e.g. potassium hydroxide, sodium ethylate, potassium t-butylate) in an inert organic solvent such as dimethyl sulphoxide, ethanol, diethylene glycol or triethylene glycol and subsequently the hydrazone formed can be decomposed at elevated temperature. A preferred variant is the reaction according to the Huang-Minlon process, i.e. heating the compound of formula XXXIXa under reflux in a high-boiling solvent which is miscible with water (e.g. diethylene glycol or triethylene glycol) together with hydrazine hydrate and potassium hydroxide, subsequently distilling off the water until the hydrazone has decomposed and boiling the mixture under reflux until the reduction has finished. Further, the compounds of formula XXXIXa can be reduced by heating with amalgamated zinc and hydrochloric acid; if desired, an organic solvent such as ethanol, acetic acid, dioxan or toluene can be added to the reaction mixture.

The reaction of the compounds of formula LV with Grignard reagents in accordance with process variant h) can be carried out in a manner known per se. Halomethyl preferably stands for iodomethyl. The alkenylmagnesium bromides are the preferred alkenylmagnesium halides. The reaction is conveniently carried out in an inert organic solvent, for example an ether such as diethyl ether, tetrahydrofuran or dioxan in the presence of a base such as methyl lithium, butyl lithium and the like. The temperature and pressure are not critical; the reaction is, however, preferably carried out at atmospheric pressure and a temperature of about −80° C. to room temperature. The hydrolysis of the reaction mixture can also be carried out according to known methods, for example with water or ammonium chloride solution.

The compounds of formulae II, IV, VII and IX in which $R^1$ signifies alkyl and the compounds of formula VIII are known compounds or analogues of known compounds.

The compounds of formula XXXIXa are novel and are also an object of the present invention. They can be prepared according to methods known per se, for example by reacting the corresponding compounds which have a cyano group in place of the alkenoyl group with a (2E-alkenyl)magnesium bromide or a (3-alkenyl)magnesium bromide.

The compounds of formulae II, IV, VII and IX in which $R^1$ is different from alkyl and the compounds of formulae III, V, VI, X and LV are also novel. The preparation of these compounds is illustrated on the basis of representative examples in the following Reaction Schemes 1-7 in which R signifies hydrogen or alkyl, $R^3$ signifies alkyl and $R^4$ signifies 1E-alkenyl, 2Z-alkenyl, 3E-alkenyl or 4-alkenyl.

Scheme 1

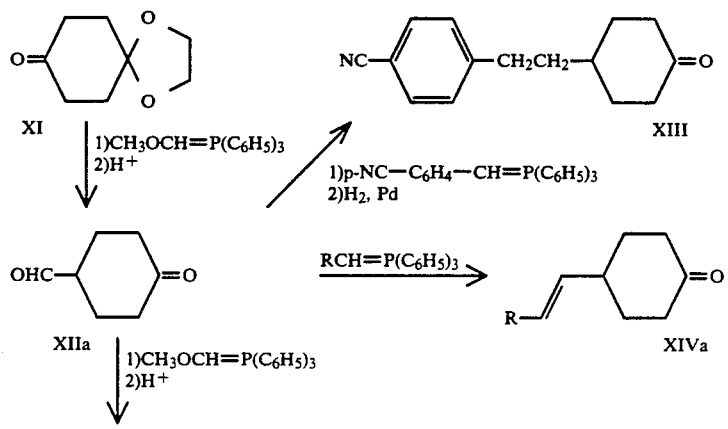

Scheme 1
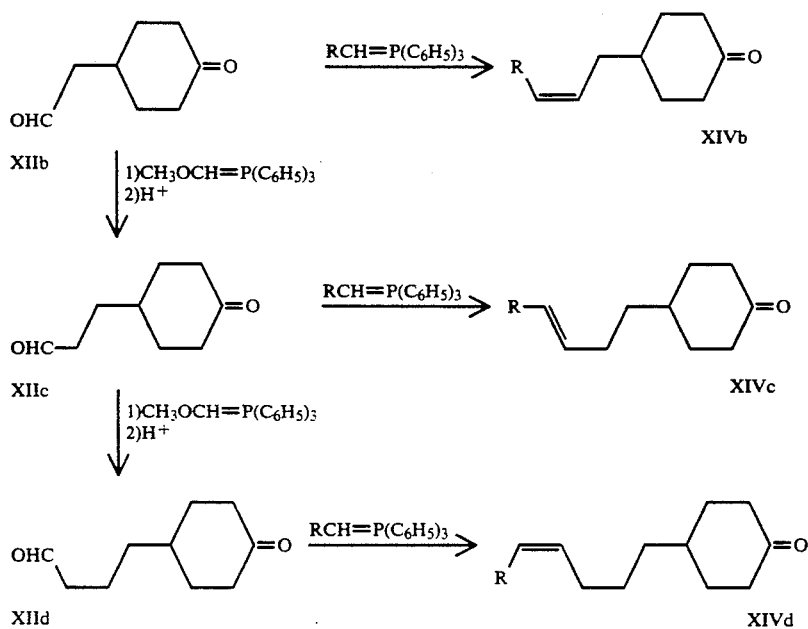
Scheme 2
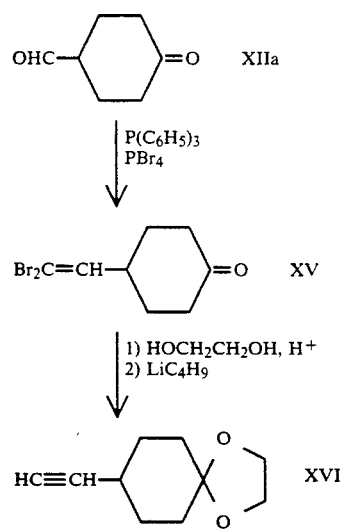
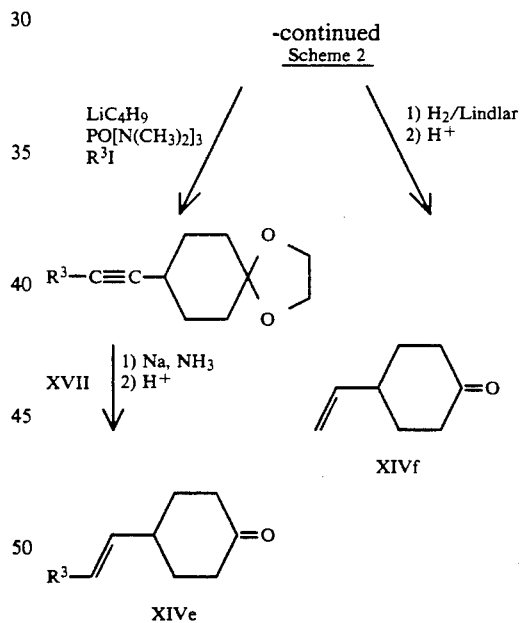
Scheme 3
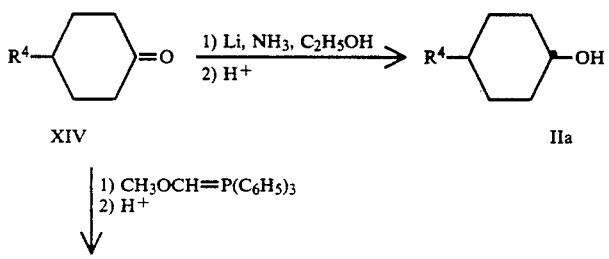

Scheme 3
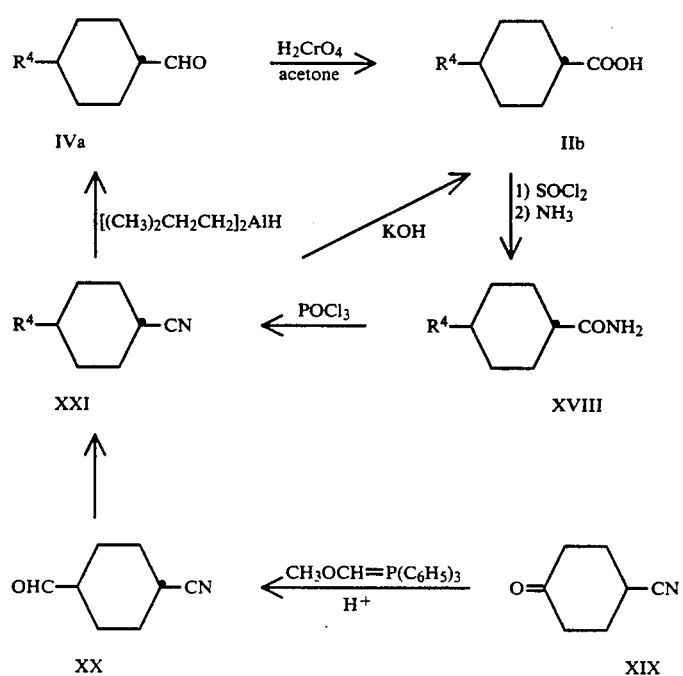
Scheme 4
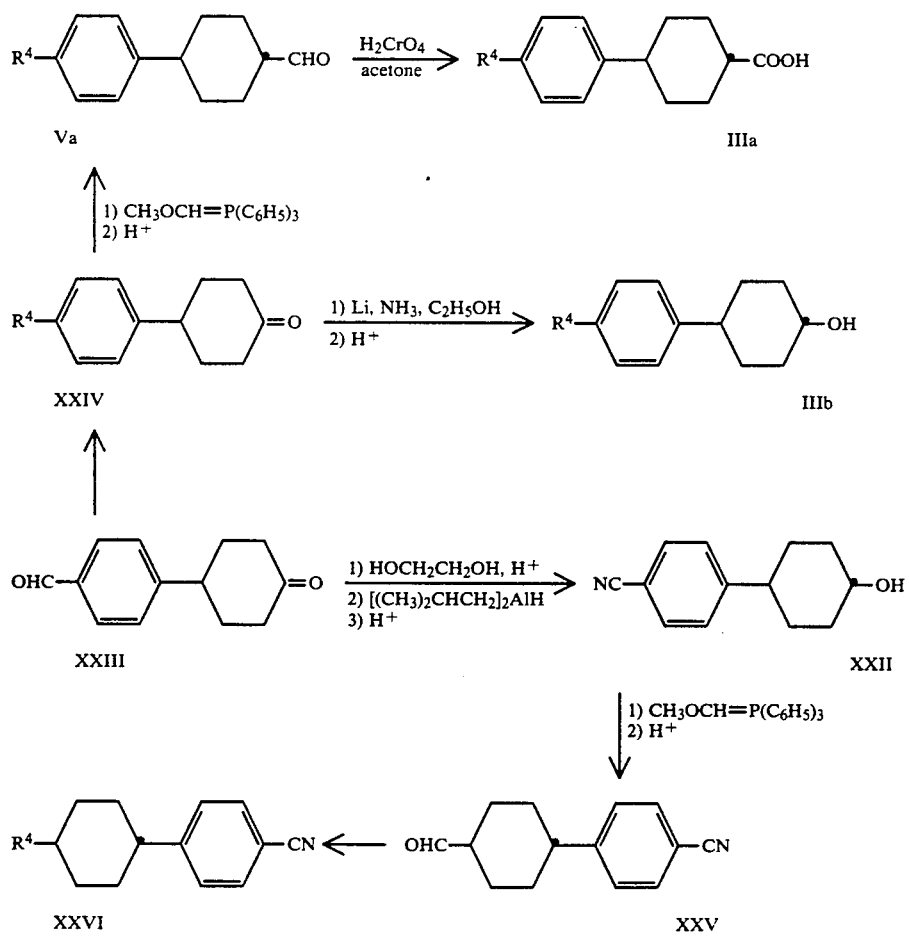

-continued
Scheme 4
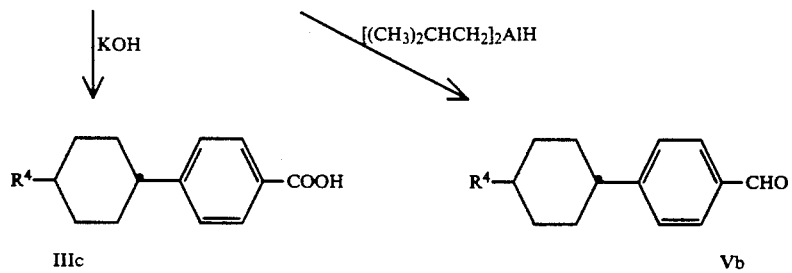
Scheme 5
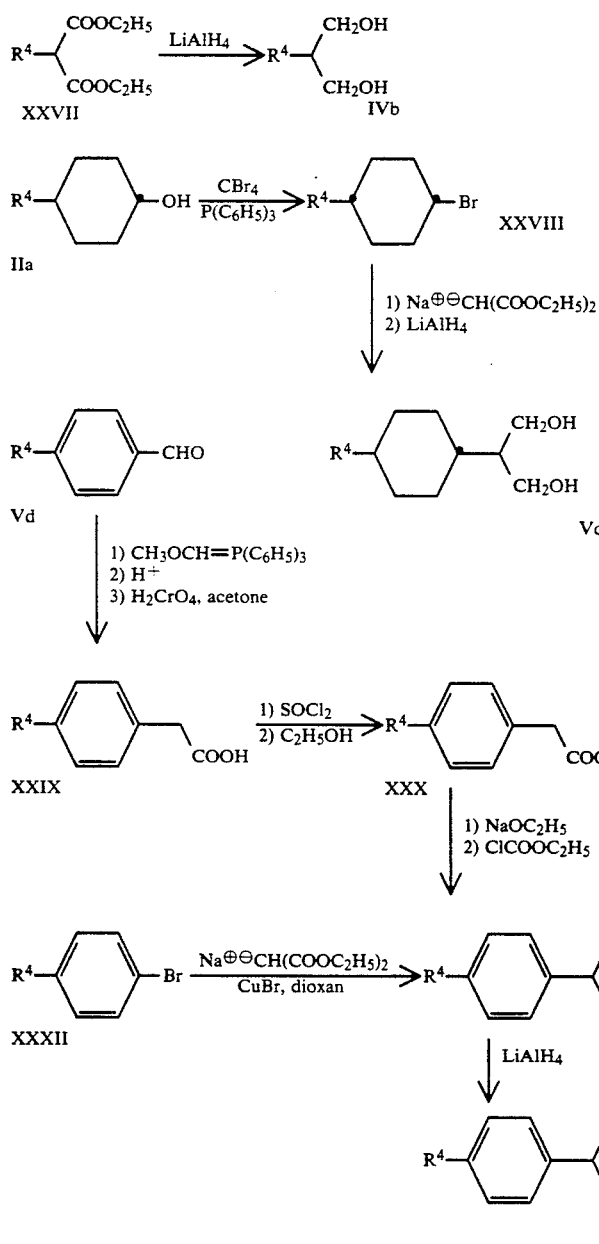

Scheme 6
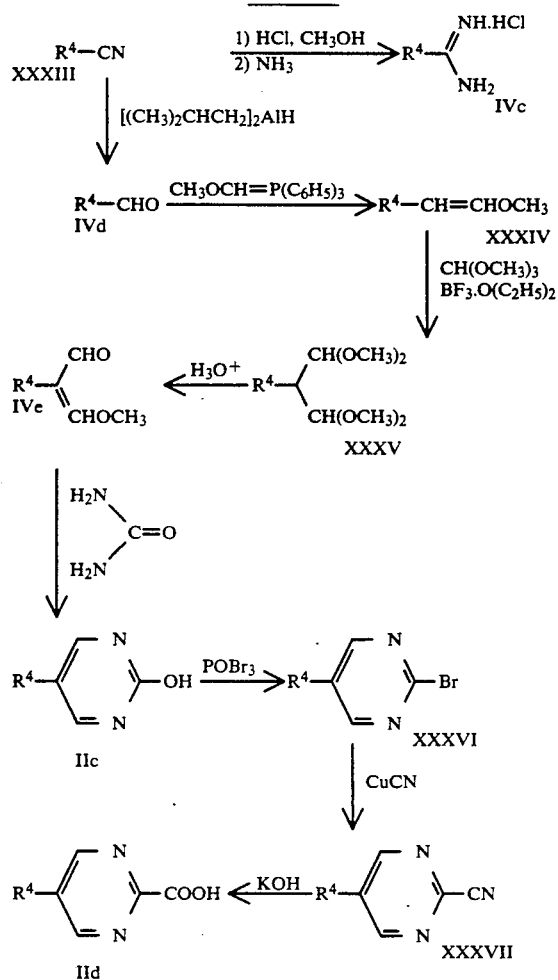
Scheme 7
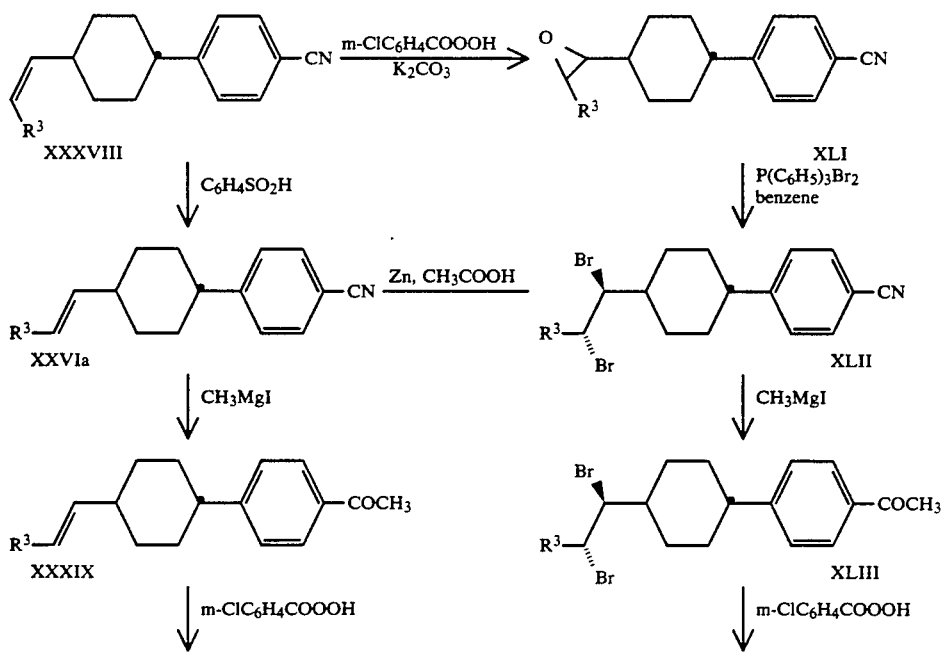

Scheme 7

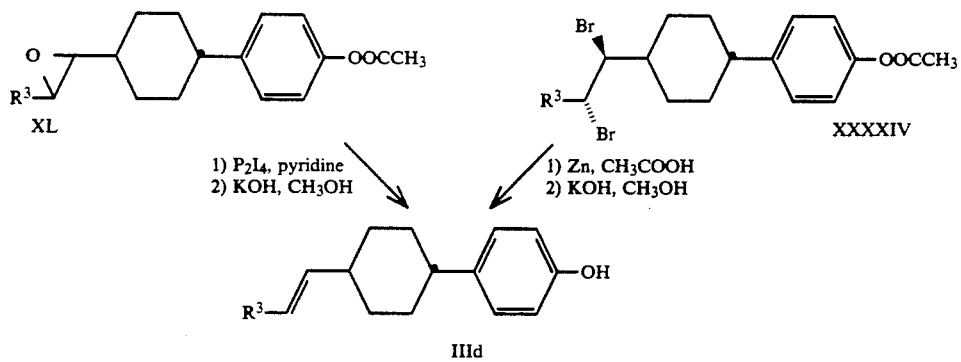

IIId

The compounds of formula XIII can be converted into the corresponding alkenyl compounds in an analogous manner to Scheme 3.

The introduction of the alkenyl groups in accordance with XX→XXI, XXIII→XXIV and XXV→XVI can be carried out in an analogous manner to the method described in Scheme 1. Further alternatives for the introduction of alkenyl groups are illustrated in Examples 19-22 hereinafter.

Alkenylphenols can be obtained, for example, by reacting p-hydroxybenzaldehyde with (2-methoxyethoxy)methyl chloride (protection of the hydroxy group), subsequently introducing the alkenyl group according to the method described in Scheme 1 and cleaving off the protecting group by means of zinc bromide.

4'-Cyano-4-biphenylcarboxaldehyde can be obtained, for example, by reacting 4-bromobiphenyl firstly with $Cl_2CHOCH_3$ and titanium tetrachloride and then with water and converting the bromo-aldehyde obtained with copper(I) cyanide in dimethylformamide into the cyanoaldehyde. This can then be further reacted, for example, in an analogous manner to Scheme 3.

The halomethyl derivatives of formula LV can be obtained, for example, from the corresponding aldehydes by reduction with sodium borohydride, reaction of the hydroxymethyl derivative with p-tosyl chloride and conversion of the tosylate into the halide, e.g. with sodium iodide in acetone.

In the above reactions there are obtained in certain cases mixtures of cis trans-isomeric cyclohexane derivatives which, however, can be separated in a manner known per se, e.g. by chromatography and/or crystallization.

Further, there are obtained in certain cases E/Z-mixtures of alkenyl compounds, especially when the alkenyl groups are introduced by a Witting reaction in accordance with Schemes 1, 3 and 4 and in accordance with process variant d). Such mixtures can also be separated according to methods known per se, e.g. by chromatography. In this case, silica gel impregnated with silver nitrate has been found to be especially advantageous. If desired, Z-isomers can be converted into a mixture containing predominantly the E-form by equilibration with sulphinic acids, e.g. benzenesulphinic acid or p-toluenesulphinic acid. Further, for example, the Z-form or E-form can be converted into the E-form or Z-form by reaction with a peracid (e.g. m-chloroperbenzoic acid) in the presence of potassium carbonate, halogenation of the epoxide with triphenylphosphine-bromine in benzene and reduction of the bromide with zinc in glacial acetic acid. On the other hand, the configuration is retained, for example, when an alkenyl compound is oxidized with a peracid (e.g. m-chloroperbenzoic acid) and the epoxide is reduced with diphosphortetraiodide in pyridine or when an alkenyl compound is halogenated with bromine in methylene chloride and the bromide is reduced with zinc in glacial acetic acid. Such reactions are illustrated in Scheme 7 above and are described in detail e.g. by P. E. Sonnet in Tetrahedron 36, 557-604 (1980). They can be used with advantage for optimizing the yield with respect to the desired isomers.

In process variants a, b, c, e, f, g and h there are conveniently used starting materials in which the alkenyl group is already present in the desired configuration.

The Wittig Reaction in accordance with process variant d generally gives a mixture in which the corresponding Z-alkenyl compound is predominantly present. For the manufacture of the compounds of formula I in which $R^1$ and $R^2$ signify Z-alkenyl residues, an isomerization can therefore generally be omitted. For the manufacture of the compounds of formula I in which one of the residues $R^1$ and $R^2$ signifies E-alkenyl and the other signifies Z-alkenyl, the E-alkenyl residue is preferably introduced first (optionally via isomerization of the Z-alkenyl residue) and then the reaction in accordance with process variant d) is carried out. However, the Z-alkenyl residue can be introduced first and this can be protected, for example as the dibromide (by reaction with bromine), during an isomerization of the other alkenyl residue which may be carried out. For the manufacture of the compounds of formula I in which $R^1$ and $R^2$ signify E-alkenyl residues, the isomerization of the two alkenyl residues can be carried out preferably as a final step. However, an already present E-alkenyl residue can, if desired, be protected as the dibromide during the isomerization of the other residue. Of course, in all cases simply a chromatographical separation of the isomer mixture obtained can also be carried out.

In the reaction of the compounds of formula XL (Scheme 7) it can be of advantage firstly to saponify the ester group, then to etherify the epoxy-phenol obtained with a compound of formula VIII in an analogous manner to process variant e) and finally to reduce the epoxy group with diphosphortetraiodide in pyridine.

The compounds of formulae IX and X can be obtained in an analogous manner to the methods described above, for example from nitro-aldehydes or nitro-ketones (e.g. p-nitro-benzaldehyde, 4-(p-nitrophenyl)-cyclohexanone) by optional chain-lengthening at the aldehyde or ketone group and alkenylation in an analogous manner to Schemes 1, 3 and 4. The isomerization of a Z-alkenyl group can be carried out, for example, by reaction with N-bromosuccinimide in trifluoroacetic acid and subsequent heating with sodium iodide in dimethylformamide. Further, equilibration with benzenesulphinic acid or reaction with diphenyl disulphide under the influence of light are also suitable.

The compounds in accordance with the invention can be used in the form of mixtures with one another and/or with other liquid crystal components such as e.g. with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, terphenyls, phenylcyclohexanes, cyclohexylbiphenyls, phenylpyrimidines, diphenylpyrimidines, cyclohexylphenylpyrimidines, phenyldioxanes, 2-cyclohexyl-1-phenylethanes and the like. Such substances are known to the person skilled in the art and many of them are, moreover, commercially obtainable.

Having regard to the favourable properties of the compounds in accordance with the invention their amount in liquid crystalline mixtures can vary in wide limits and can amount to up to 100%. The mixtures in accordance with the invention conveniently contain at least about 1 wt. % and preferably about 10-90 wt. % of compounds of formula I.

Preferred components which can be used in admixture with one or more compounds of formula I are the compounds of the following general formulae:

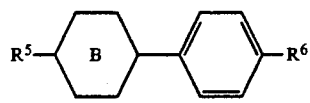

VL

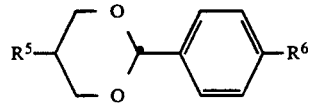

VLI

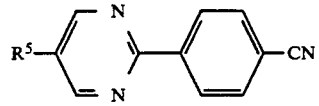

VLII

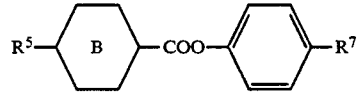

VLIII

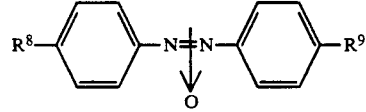

IL

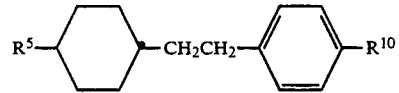

L

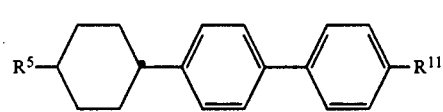

LI

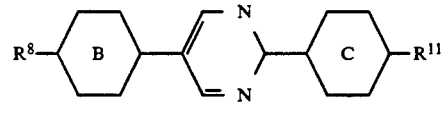

LII

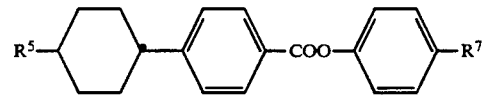

LIII

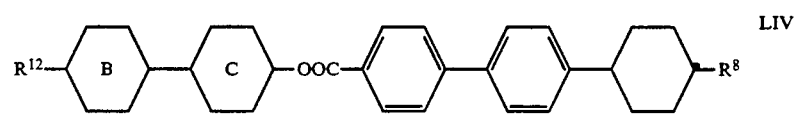

LIV wherein the rings B and C represent 1,4-phenylene or trans-1,4-cyclohexylene; $R^5$ signifies alkyl, 3E-alkenyl, 4-alkenyl or on a cyclohexane ring also 2Z-alkenyl or on a cyclohexane or m-dioxane ring also 1E-alkenyl; $R^6$ denotes alkyl, alkoxy, —CN or —NCS; $R^7$ represents alkyl or alkoxy; $R^8$ and $R^9$ signify alkyl; $R^{10}$ represents cyano, alkyl, alkoxy, p-alkylphenyl, p-alkoxyphenyl, trans-4-alkyl-cyclohexyl, 4'-alkyl-4-biphenylyl, p-(trans-4-alkylcyclohexyl)-phenyl, 2-(trans-4-alkylcyclohexyl)ethyl, p-[2-(trans-4-alkylcyclohexyl)ethyl]-phenyl or 2-[p-(trans-4-alkylcyclohexyl)phenyl]ethyl; $R^{11}$ denotes cyano or alkyl; $R^{12}$ signifies alkyl, 3E-alkenyl or on a cyclohexane ring also 1E-alkenyl; and the alkyl, alkoxy and alkenyl residues in $R^5$, $R^6$, $R^7$, $R^8$, $R^9$, $R^{10}$, $R^{11}$ and $R^{12}$ are straight-chain residues with a maximum of 7 carbon atoms.

The mixtures in accordance with the invention can also contain optically active compounds (for example optically active biphenyls) and/or dichroic colouring substances (for example azo, azoxy or anthraquinone colouring substances). The amount of such compounds is determined by the solubility and the desired pitch, colour, extinction and the like. Preferably, the amount of optically active compounds amounts to a maximum of about 4 wt. % and the amount of dichroic colouring substances amounts to a maximum of about 10 wt. % in the total mixture.

The manufacture of the mixtures in accordance with the invention can be carried out in a manner known per se, e.g. by heating a mixture of the components to a temperature barely above the clearing point and subsequently cooling down. The manufacture of an electro-optical device can also be carried out in a manner known per se, e.g. by evacuating a suitable cell and introducing the mixture into the evacuated cell.

The compounds of formulae VL-VLIII, L, LI, LIII and LIV in which $R^5$ or $R^{12}$ signifies alkenyl are novel. They can be prepared according to the methods described above.

The manufacture of the compounds in accordance with the invention is illustrated further by the following Examples. C signifies a crystalline phase, S signifies a smectic phase, $S_B$ signifies a smectic B phase, N signifies a nematic phase and I signifies the isotropic phase. Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C.), normal pressure is about 1 atmosphere and room temperature is about 23° C. The petroleum ether is a well known mixture of low-boiling hydrocarbons. Unless otherwise indicated the Examples were carried out as written.

Example 1 a) 261.2 g of methoxymethyl-triphenylphosphonium chloride were suspended in 550 ml of t-butyl methyl ether and the suspension was treated at −10° C. with 90.53 g of potassium t-butylate. The cooling bath was removed and the mixture was stirred for a further 1 hour at room temperature. The suspension was subsequently treated slowly at −10° C. with a solution of 70 g of 4,4-ethylenedioxycyclohexanone in 350 ml of tetrahydrofuran, the mixture was stirred for a further 1 hour at room temperature, then treated with water and extracted three times with diethyl ether. The organic phases were washed twice with water and the aqueous phases were back-extracted with diethyl ether. The combined organic phases were dried over magnesium sulphate and concentrated. The crystalline residue obtained was dissolved in ethyl acetate, diluted with petroleum ether, filtered and freed from solvent. Distillation of the yellow oil obtained (100 g) gave in the main run (71° C./0.20-0.17 Torr) 75.28 g (91.17%) of 1,1-ethylenedioxy-4-(methoxymethylene)cyclohexane as a clear, colourless liquid.

b) A mixture of 10.55 g of 1,1-ethylenedioxy-4-(methoxymethylene)cyclohexane, 130 ml of water and 200 ml of glacial acetic acid was heated to reflux for 1 hour. The solvent was subsequently distilled off on a rotary evaporator and the distillate was extracted twice with methylene chloride. The distillation residue (a yellow oil) was diluted with 200 ml of water, neutralized with sodium carbonate solution and extracted three times with methylene chloride. The organic phases were washed with saturated sodium carbonate solution and the aqueous phases were back-extracted with methylene chloride. The organic phases were dried over magnesium sulphate and evaporated. Distillation of the residual, yellow oil gave, at 70° C./0.15 Torr, 6.7 g (93%) of 4-formylcyclohexanone.

EXAMPLE 2 a) A solution of 36.72 g of triphenylphosphine in 200 ml of methylene chloride was treated slowly at −20° C. with 23.22 g of carbon tetrabromide and the mixture was stirred for a further 10 minutes. The mixture was subsequently added dropwise by means of a cannula to a solution, cooled to −60° C., of 6.30 g of 4-formylcyclohexanone in 100 ml of methylene chloride. The reaction mixture was stirred for a further 15 minutes at −60° C. and then partitioned in water/methylene chloride. The aqueous phases were extracted twice with methylene chloride. The organic phases were washed twice with water, dried over magnesium sulphate and evaporated. Low-pressure chromatography of the pale yellow oil obtained (16 g) on silica gel with ethyl acetate/petroleum ether (vol. 10:90) gave 12.08 g (85.8%) of 4-(2,2-dibromovinyl)cyclohexanone as a pale yellow liquid.

b) A mixture of 2 g of 4-(2,2-dibromovinyl)cyclohexanone, 3.43 g of ethylene glycol, 0.202 g of p-toluenesulphonic acid and 240 ml of benzene was boiled at reflux for 5 hours with the separation of water. The reaction mixture was subsequently treated with potassium carbonate, stirred briefly and left to stand overnight. Thereafter, the mixture was filtered and the filtrate was freed from solvent on a rotary evaporator. The residue was taken up in 200 ml of methylene chloride and the solution was washed twice with dilute sodium hydroxyde solution and once with water. The aqueous phases were back-extracted with methylene chloride. The organic phases were dried over magnesium sulphate, filtered and evaporated. There were thus obtained 14 g of 1,1-ethylenedioxy-4-(2,2-dibromovinyl)cyclohexane as a light yellow, crystallizing liquid.

c) A solution of 14 g of 1,1-ethylenedioxy-4-(2,2-dibromovinyl)cyclohexane in 70 ml of tetrahydrofuran was cooled to −20° C. and treated slowly at this temperature with 76.62 ml of a 1.4M solution of butyl lithium in hexane (exothermic reaction). The cooling bath was removed and the mixture was left to warm to 20° C. within about 20 minutes. The reaction mixture was subsequently treated with 150 ml of water and extracted three times with diethyl ether. The organic phases were washed twice with water and the wash-water was back-extracted with diethyl ether. The organic phases were dried over magnesium sulphate, filtered and evaporated. Low-pressure chromatography of the residual, yellow liquid (8 g) on silica gel with ethyl acetate/petroleum ether (vol. 7:93) gave 6.5 g (91%) of 4-ethynyl-1,1-ethylenedioxycyclohexane as a clear liquid.

d) A solution of 6.5 of 4-ethynyl-1,1-ethylenedioxycyclohexane in 40 ml of tetrahydrofuran was treated at −20° C. with 39.1 ml of a 1.4M solution of butyl lithium in hexane. The mixture was subsequently treated at 0° C. with 60 ml of hexamethylphosphoric acid triamide (brief temperature increase to 26° C.) and then dropwise with 6.5 ml of propyl iodide. The cooling bath was removed and the mixture was left to warm to room temperature. A white precipitate formed. After 30 minutes the reaction mixture was treated with 150 ml of water and extracted three times with hexane. The organic phases were washed three times with water and the wash-water was back-extracted with hexane. The organic phases were dried over magnesium sulphate, filtered and freed from solvent on a rotary evaporator. Low-pressure chromatography of the yellow liquid obtained (9 g) on silica gel with ethyl acetate/petroleum ether (vol. 10:90) and treatment with active carbon gave 6.23 g (76.5%) of 1,1-ethylenedioxy-4-(1-pentynyl)cyclohexane as a slightly pale yellow liquid.

e) A solution of 4.5 g of 1,1-ethylenedioxy-4-(1-pentynyl)cyclohexane in 54 ml of tetrahydrofuran was treated dropwise with about 50 ml of pre-condensed ammonia in a sulphonation flask equipped with magnetic stirrer. The mixture was subsequently treated portionwise at −78° C. within 7 hours with 1.3 g of sodium. 1.5 hours after the last addition the ammonia was evaporated off and the reaction mixture was neutralized with 25% hydrochloric acid and left to stand overnight. Thereafter, the reaction mixture was partitioned three times in water/diethyl ether. The aqueous phases were back-extracted with diethyl ether. The organic phases were dried over magnesium sulphate and freed from solvent on a rotary evaporator. The pale yellow liquid obtained (3.8 g) was treated with 200 ml of acetone and 0.1 ml of concentrated sulphuric acid. The mixture was heated to reflux for 10 minutes, then treated with water and freed from acetone on a rotary evaporator. The residue was partitioned three times in methylene chloride/water. The aqueous phases were back-extracted with methylene chloride. The organic phases were dried over magnesium sulphate and evaporated. Chromatographic separation of the residual, yellow liquid (3.5 g) on silica gel with ethyl acetate/petroleum ether (vol. 7:93) gave 3.0 g (83.5%) of 4-(1E-pentenyl)cyclohexanone as a pale yellow liquid.

EXAMPLE 3

1.63 g of 4-(1E-pentenyl)cyclohexanone were dissolved in 8 ml of diethyl ether and 14 ml of ethanol. The solution was subsequently treated dropwise with about 70 ml of ammonia and the mixture was treated portionwise with lithium wire until the colour of the reaction mixture remained constant for 1.5 hours (about 1.3 g of lithium). Thereafter, the ammonia was evaporated off and the mixture was made acid with ammonium chloride and hydrochloric acid and left to stand for 3 days. The reaction mixture was then partitioned in diethyl ether/water and the aqueous phases were back-extracted with diethyl ether. The organic phases were dried over magnesium sulphate, filtered and freed from solvent on a rotary evaporator. Low-pressure chromatography of the residual, yellow oil on silica gel with ethyl acetate/petroleum ether (vol. 10:90) gave 1.47 g (89.1%) of trans-4-(1E-pentenyl)cyclohexanol as a light yellow, viscous oil.

The following compound was prepared in an analogous manner:

trans-4-(1E-Butenyl)cyclohexanol.

EXAMPLE 4 a) 7 g of methoxymethyl-triphenylphosphonium chloride were suspended in 35 ml of t-butyl methyl ether and the suspension was treated at −20° C. with 2.43 g of potassium t-butylate. The mixture was stirred for a further 1 hour at room temperature, then treated dropwise at −20° C. with a solution of 2 g of 4-(1E-pentenyl)cyclohexanone in 18 ml of tetrahydrofuran and the mixture was stirred for a further 1 hour at room temperature. The reaction mixture was subsequently treated with water and extracted three times with 50 ml of diethyl ether each time. The extracts were washed with water and the wash-water was back-extracted with diethyl ether. The organic phases were dried over magnesium sulphate and freed from solvent. The residue was dissolved in ethyl acetate and the solution was diluted with petroleum ether, freed from precipitated triphenylphosphine oxide by filtration and the filtrate was concentrated. This procedure for the separation of triphenylphosphine oxide was repeated twice and the crude product of 1-(methoxymethylene)-4-(1E-pentenyl)cyclohexane obtained was processed without additional purification.

b) 2.75 g of 1-(methoxymethylene)-4-(1E-pentenyl)cyclohexane (crude product from paragraph a) were heated to boiling for 30 minutes with 100 ml of tetrahydrofuran/2N hydrochloric acid (vol. 4:1) and then stirred overnight at room temperature. The mixture was subsequently treated with 100 ml of water and extracted three times with 100 ml of diethyl ether each time. The extracts were washed with dilute sodium hydrogen carbonate solution and water and the aqueous phases were back-extracted with diethyl ether. The organic phases were dried over magnesium sulphate and evaporated. Low-pressure chromatography of the residual yellowish liquid (2.5 g) on silica gel with petroleum ether and ethyl acetate/petroleum ether (vol. 3:97) gave 1.65 g (76%) of 4-(1E-pentenyl)cyclohexanecarboxaldehyde.

c) A solution of 1.6 g of 4-(1E-pentenyl)cyclohexanecarboxaldehyde in 120 ml of acetone was cooled to −10° C., treated dropwise with 8N chromic acid (about 10 ml) until the colour of the reaction mixture remained brown-orange and the mixture was stirred for a further 1 hour. Excess chromic acid was reduced by adding isopropanol. The green solution was subsequently partitioned three times in water/methylene chloride. The organic extracts were washed twice with water and the wash-water was back-extracted with methylene chloride. The organic phases were dried over magnesium sulphate and evaporated. The pale brown crystalline residue (2.01 g) was dissolved partially in 20 ml of petroleum ether. Undissolved residue was filtered off and the filtrate was evaporated. Recrystallization of the residue obtained from 60 ml of petroleum ether at −78° C. gave 866 mg (49.5%) of 4-(1E-pentenyl)cyclohexanecarboxylic acid as white crystals.

d) A mixture of 1.29 g of 4-(1E-pentenyl)cyclohexanecarboxylic acid and 20 ml of a 11 percent (wt./vol.) solution of potassium hydroxide in diethylene glycol was boiled at reflux for 20 hours while gassing with argon. The reaction mixture was subsequently made slightly acid with 25 percent hydrochloric acid and partitioned three times in water/ethylene chloride. The organic extracts were washed twice with water and the wash-water was back-extracted with methylene chloride. The organic phases were dried over magnesium sulphate and freed from solvent on a rotary evaporator. Recrystallization of the dark brown, crystallizing oil obtained (1.17 g) from 50 ml of petroleum ether at −78° C. gave 0.44 g of trans-4-(1E-pentenyl)cyclohexanecarboxylic acid as pale brown crystals. The mother liquor containing 0.695 g of crude cis/trans-4-(1-E-pentenyl)-cyclohexanecarboxylic acid was not worked-up.

The following compound was prepared in an analogous manner:
trans-4-(1E-Butenyl)cyclohexanecarboxylic acid.

EXAMPLE 5 a) 10.4 g of methoxymethyl-triphenylphosphonium chloride were suspended in 60 ml of t-butyl methyl ether while gassing with argon in a sulphonation flask equipped with a thermometer, a mechanical stirrer, a dropping funnel and a solid substance addition tube and the suspension was treated with 3.6 g of solid potassium t-butylate at −10° C. within 10 minutes. After completion of the addition the mixture was stirred for a further 30 minutes at −10° C. to 0° C. and then the deep orange, heterogeneous reaction mixture was treated dropwise at 0° C. with a solution of 4.2 g of 4-(p-cyanophenyl)cyclohexanone in 50 ml of absolute tetrahydrofuran. The reaction mixture was subsequently stirred for a further 2 hours at room temperature, then poured into 500 ml of hexane and filtered. Low-pressure chromatography (0.5 bar) of the concentrated residue (7.1 g) on silica gel with ethyl acetate/petroleum ether (vol. 5:95) gave 4.5 g (94%) of p-[4-(methoxymethylene)cyclohexyl]benzonitrile as a colourless oil; purity 95%, Rf-value (ethyl acetate/petroleum ether vol. 1:9) 0.30.

b) A mixture of 4.2 g of p-[4-methoxymethylene)cyclohexyl]benzonitrile and 100 ml of tetrahydrofuran/2N hydrochloric acid (vol. 4:1) was heated to reflux for 30 minutes in a round flask. The reaction mixture was subsequently poured into 100 ml of water and extracted three times with 100 ml of diethyl ether each time. The organic phases were washed once with 100 ml of water, dried over magnesium sulphate and concentrated. There were obtained 3.9 g (100%) of 4-(p-cyanophenyl)cyclohexanecarboxaldehyde as a colourless oil which was used in the next step without further purification; trans/cis ratio about 3:1, Rf-value (ethyl acetate/petroleum ether vol. 3:7) 0.41. By crystallization from hexane there could be obtained pure trans-4-(p-cyanophenyl)cyclohexanecarboxaldehyde; m.p. 57.1° C.

c) A suspension of 29.0 g of methoxymethyl-triphenylphosphonium chloride in 200 ml of t-butyl methyl ether was treated within 10 minutes with 9.7 g of potassium t-butylate while gassing with argon at −10° C. and the mixture was stirred for a further 1 hour. The mixture was then treated dropwise within 15 minutes at −10° C. with a solution of 12.0 g of trans-4-(p-cyanophenyl)cyclohexanecarboxaldehyde in 90 ml of t-butyl methyl ether and the resulting mixture was stirred for a further 1 hour at 0° C. The reaction mixture was subsequently poured into 150 ml of water and extracted three times with 150 ml of diethyl ether each time. The organic phases were washed twice with 100 ml of water each time, dried over magnesium sulphate and concentrated. The resulting, viscous oil was dissolved in 20 ml of ethyl acetate and the clear solution was diluted with 300 ml of petroleum ether and left to stand for 10 minutes at −20° C. The precipitated triphenylphosphine oxide was subsequently filtered off and the filtrate was concentrated to dryness. Low-pressure chromatography (0.5 bar) of the residue (16.3 g) on silica gel with ethyl acetate/petroleum ether (vol. 5:95) gave 10.1 g (74%) of p-[trans-4-(2-methoxyvinyl)cyclohexyl]benzonitrile as colourless crystals; Rf-value (ethyl acetate/petroleum ether vol. 10:90) 0.32.

d) A solution of 10.1 g of p-[trans-4-(2-methoxyvinyl)cyclohexyl]benzonitrile in 200 ml of tetrahydrofuran/2N hydrochloric acid (vol. 4:1) was heated to reflux for 1 hour. The reaction mixture was subsequently poured into 200 ml of water and extracted three times with 150 ml of diethyl ether each time. The organic phases were washed twice with 100 ml of water each time, dried over magnesium sulphate and concentrated, whereby 9.8 g of [trans-4-(p-cyanophenyl)cyclohexyl]acetaldehyde were obtained as light yellowish crystals (purity 98.7%). Recrystallization of a sample from hexane/t-butyl methyl ether (vol. 1:1) gave pure aldehyde with m.p. 43.4° C.

e) A suspension of 4.5 g of methoxymethyl-triphenylphosphonium chloride in 40 ml of t-butyl methyl ether was treated within 3 minutes with 1.5 g of potassium t-butylate while gassing with argon at −10° C. and the solution was stirred for a further 1 hour at 0°-5° C. The suspension was then treated dropwise within 5 minutes at 0° C. with a solution of 2.0 g of [trans-4-(p-cyanophenyl)cyclohexyl]-acetaldehyde in 20 ml of t-butyl methyl ether and the mixture was stirred for a further 2 hours at room temperature. The reaction mixture was subsequently poured into 100 ml of water and extracted three times with 100 ml of diethyl ether each time. The organic phases were washed twice with 100 ml of water each time, dried over magnesium sulphate and concentrated. The resulting, viscous oil was dissolved in 15 ml of ethyl acetate and the clear solution was treated with 250 ml of petroleum ether. After leaving to stand for 10 minutes at −20° C. the precipitated triphenylphosphine oxide was filtered off and the filtrate was concentrated to dryness. Low-pressure chromatography (0.5 bar) of the residue (3.3 g) on silica gel with ethyl acetate/petroleum ether (vol. 5:95) gave 2.04 g (91%) of p-[trans-4-(3-methoxy-2-propenyl)cyclohexyl]benzonitrile as a colourless oil; Rf-value (ethyl acetate/petroleum ether vol. 10:90) 0.33.

f) A solution of 2.04 g of p-[trans-4-(3-methoxy-2-propenyl)cyclohexyl]benzonitrile in 100 ml of tetrahydrofuran/2N hydrochloric acid (vol. 4:1) was heated to reflux for 1 hour. The reaction mixture was subsequently poured into 100 ml of water and extracted three times with 100 ml of diethyl ether each time. The organic phases were washed twice with 100 ml of water each time, dried over magnesium sulphate and concentrated, whereby 1.9 g (99%) of 3-[trans-4-(p-cyanophenyl)cyclohexyl]propionaldehyde were obtained as colourless crystals; Rf-value (ethyl acetate/petroleum ether vol. 10:90) 0.15.

g) A suspension of 6.4 g of methoxymethyl-triphenylphosphonium chloride in 80 ml of t-butyl methyl ether was treated within 3 minutes with 2.1 g of potassium t-butylate while gassing with argon at 0° C. and the mixture was stirred for a further 1 hour at 0°-5° C. The mixture was then treated dropwise within 5 minutes at 0° C. with a solution of 3.0 g of 3-[trans-4-(p-cyanophenyl)cyclohexyl]propionaldehyde in 20 ml of t-butyl methyl ether and the resulting mixture was stirred for a further 2 hours at room temperature. The reaction mixture was subsequently poured into 100 ml of water and extracted three times with 100 ml of diethyl ether each time. The organic phases were washed twice with 100 ml of water each time, dried over magnesium sulphate and concentrated. The residue was dissolved in 15 ml of ethyl acetate and the clear solution was treated with 250 ml of petroleum ether. After leaving to stand for 10 minutes at −20° C. the precipitated triphenylphosphine oxide was filtered off and the filtrate was concentrated to dryness. Low-pressure chromatography (0.5 bar) of the residue (5.5 g) on silica gel with ethyl acetate/petroleum ether (vol. 5:95) gave 2.95 g (88%) of p-[trans-4-(4-methoxy-3-butenyl)cyclohexyl]benzonitrile as colourless crystals.

h) A solution of 2.95 g of p-[trans-4-(4-methoxy-3-butenyl)cyclohexyl]benzonitrile in 100 ml of tetrahydrofuran/2N hydrochloric acid (vol. 4:1) was heated to reflux for 15 minutes. The reaction mixture was subsequently poured into 100 ml of water and extracted three times with 100 ml of diethyl ether each time. The organic phases were washed twice with 100 ml of water each time, dried over magnesium sulphate and concentrated, whereby 2.6 g (93%) of 4-[trans-4-(p-cyanophenyl)cyclohexyl]butyraldehyde were obtained as a slightly yellowish oil; Rf-value (toluene/ethyl acetate vol. 95:5) 0.23.

The following compounds were prepared in an analogous manner:
4-cyanocyclohexanecarboxaldehyde,
(4-cyanocyclohexyl)acetaldehyde,
3-(4-cyanocyclohexyl)propionaldehyde,
4-(4-cyanocyclohexyl)butyraldehyde,
trans-4-(4'-cyano-4-biphenylyl)cyclohexanecarboxaldehyde,
[trans-4-(4'-cyano-4-biphenylyl)cyclohexyl]acetaldehyde,
3-[trans-4-(4'-cyano-4-biphenylyl)cyclohexyl]propionaldehyde,
4-[trans-4-(4'-cyano-4-biphenylyl)cyclohexyl]butyraldehyde.

EXAMPLE 6 a) 10.0 g of 4'-bromo-4-biphenylcarboxaldehyde and 5.31 g of copper(I) cyanide were dissolved in 80 ml of dimethylformamide while gassing with argon and the solution was heated to reflux for 15 hours at 180° C. bath temperature. Thereafter, the reaction mixture was poured cautiously into 200 ml of 25 percent ammonia and extracted three times with 200 ml of methylene chloride each time. The organic phases were washed once with 200 ml of 25 percent ammonia and twice with 200 ml of water each time, dried over magnesium sulphate and concentrated. Low-pressure chromatography (0.5 bar) of the yellowish, crystalline residue (8.7 g) on silica gel gave 5.85 g (74%) of 4'-cyano-4-biphenylcarboxaldehyde as slightly yellowish crystals; Rf-value (toluene/ethyl acetate vol. 90:10) 0.27.

b) A suspension of 12.4 g of methoxymethyl-triphenylphosphonium chloride in 120 ml of t-butyl methyl ether was treated within 3 minutes with 4.1 g of potassium t-butylate while gassing with argon at 0° C. and the mixture was stirred for a further 1 hour at 0° C. Thereafter, the mixture was treated within 10 minutes with a solution of 5.0 g of 4'-cyano-4-biphenylcarboxaldehyde in 40 ml of tetrahydrofuran and the resulting mixture was stirred for a further 1.5 hours at room temperature. The reaction mixture was subsequently poured into 200 ml of water and extracted three times with 150 ml of diethyl ether each time. The organic phases were washed twice with 150 ml of water each time, dried over magnesium sulphate and concentrated. The residue obtained was dissolved in 25 ml of ethyl acetate and the solution was treated with 350 ml of petroleum ether. After leaving to stand for 10 minutes at −20° C. the precipitated triphenylphosphine oxide was filtered off and the filtrate was concentrated to dryness. Low-pressure chromatography (0.5 bar) of the dark brown oil (9.5 g) on silica gel with ethyl acetate/petroleum ether (vol. 10:90) gave 5.2 g (91%) of 4'-(2-methoxyvinyl)-4-biphenylcarbonitrile as yellowish crystals; Rf-value (ethyl acetate/petroleum ether vol. 10:90) 0.17.

c) A mixture of 4.9 g of 4'-(2-methoxyvinyl)-4-biphenylcarbonitrile and 80 ml of glacial acetic acid/water (vol. 2:1) was heated to reflux for 1.5 hours at 100° C. bath temperature. The reaction mixture was subsequently poured into 150 ml of water and extracted three times with 100 ml of methylene chloride each time. The organic phases were washed with 100 ml of water and with 100 ml of saturated sodium hydrogen carbonate solution, dried over magnesium sulphate and concentrated. There were obtained 4.8 g of (4'-cyano-4-biphenylyl)acetaldehyde as a yellowish, crystalline residue which was processed without additional purification; Rf-value (toluene/ethyl acetate vol. 90:10) 0.37.

d) (4'-Cyano-4-biphenylyl)acetaldehyde was converted in an analogous manner to paragraph b) into 4'-(3-methoxy-2-propenyl)-4-biphenylcarbonitrile; Rf-value (ethyl acetate/petroleum ether vol. 10:90) 0.20.

e) 4'-(3-Methoxy-2-propenyl)-4-biphenylcarbonitrile was converted in an analogous manner to paragraph c) into 3-(4'-cyano-4-biphenylyl)propionaldehyde; Rf-value (toluene/ethyl acetate vol. 95:5) 0.34.

EXAMPLE 7

A suspension of 7.34 g of methyl-triphenylphosphonium bromide in 90 ml of t-butyl methyl ether was treated within 2 minutes with 2.3 g of potassium t-butylate while gassing with argon at 0° C. and the mixture was stirred for a further 1 hour at room temperature. Thereafter, the mixture was treated dropwise within 5 minutes with a solution of 3.5 g of 4-[trans-4-(p-cyanophenyl)cyclohexyl]-butyraldehyde in 20 ml of t-butyl methyl ether and the resulting mixture was stirred for a further 20 hours at room temperature. The reaction mixture was subsequently poured into 100 ml of water and extracted three times with 100 ml of diethyl ether each time. The organic phases were washed twice with 100 ml of water each time, dried over magnesium sulphate and concentrated. The residue was dissolved in 15 ml of ethyl acetate and the clear solution was treated with 250 ml of petroleum ether. After leaving to stand for 10 minutes at −20° C. the precipitated triphenylphosphine oxide was filtered off and the filtrate was concentrated to dryness. Low-pressure chromatography (0.5 bar) of the oily residue (4.8 g) on silica gel with ethyl acetate/petroleum ether (vol. 5:95) gave 3.1 g (89%) of a yellowish oil. Recrystallization at −20° C. from methanol finally gave 2.76 g (80%) of p-[trans-4-(4-pentenyl)cyclohexyl]benzonitrile as colourless crystals; m.p. (C-I) 29.8° C., cl.p. (N-I) 10.2° C.

The following compounds were manufactured in an analogous manner:

p-(trans-4-Vinylcyclohexyl)benzonitrile; m.p. (C-I) 56.4° C., cl.p. (N-I) 28.5° C.,
p-(trans-4-allylcyclohexyl)benzonitrile; m.p. (C-I) 29.2° C.,
p-[trans-4-(3-butenyl)cyclohexyl]benzonitrile; m.p. (C-N) 49.5° C., cl.p. (N-I) 52.5° C.,
4'-[trans-4-(3-butenyl)cyclohexyl]-4-biphenylcarbonitrile; m.p. (C-N) 119.2° C., cl.p. (N-I) 232.7° C.,
4'-[trans-4-(4-pentenyl)cyclohexyl]-4-biphenylcarbonitrile; m.p. (C-N) 77.4° C., cl.p. (N-I) 200.8° C.,
4'-(3-butenyl)-4-biphenylcarbonitrile; m.p. (C-I) 69.3° C., cl.p. (N-I) 45° C.,
4-(3-butenyl)cyclohexanecarbonitrile.

EXAMPLE 8 a) A suspension of 3.6 g of butyltriphenylphosphonium bromide in 40 ml of t-butyl methyl ether was placed at room temperature while gassing with argon in a sulphonation flask equipped with a thermometer, a mechanical stirrer, a dropping funnel and a solid substance addition tube, treated with 1.01 g of potassium t-butylate and stirred at room temperature for a further 1 hour. The deep orange, heterogeneous reaction mixture was subsequently cooled to −60° C. and treated within 15 minutes with a solution of 1.28 g of trans-4-(p-cyanophenyl)cyclohexanecarboxaldehyde in 10 ml of t-butyl methyl ether. The reaction mixture was stirred for a further 60 minutes while warming slowly to −30° C., then poured into 100 ml of water and extracted three times with 50 ml of diethyl ether each time. The organic phases were washed once with 50 ml of water, dried over magnesium sulphate and concentrated. Low-pressure chromatography (0.5 bar) of the residue (3.45 g) on silica gel with ethyl acetate/petroleum ether (vol. 3:97) gave 1.52 g (99%) of p-[trans-4-(1-pentenyl)cyclohexyl]benzonitrile (1E-pentenyl/1Z-pentenyl ratio about 5:95) as a colourless oil; Rf-value (ethyl acetate/petroleum ether vol. 3:97) 0.19.

b) A mixture of 1.51 g of 90 percent m-chloroperbenzoic acid and 3.0 g of ground potassium carbonate in 60 ml of methylene chloride was placed at 0° C. while gassing with argon in a sulphonation flask equipped with a thermometer, a dropping funnel and a mechanical stirrer and treated within 15 minutes with a solution of 2.0 g of p-[trans-4-(1-pentenyl)cyclohexyl]benzonitrile (1E-pentenyl/1Z-pentenyl ratio about 5:95) in 20 ml of methylene chloride. The cooling bath was subsequently removed and the reaction mixture was treated after a total of 75 minutes and 105 minutes with a further 0.75 g of 90 percent m-chloroperbenzoic acid each time. The reaction mixture was stirred for a further 60 minutes at room temperature, then poured into 50 ml of 10 percent (wt./vol.) sodium thiosulphate solution and extracted three times with 100 ml of methylene chloride each time. The organic phases were washed with 50 ml of saturated sodium hydrogen carbonate solution, dried over magnesium sulphate and concentrated. There were thus obtained 2.1 g (98%) of p-[trans-4-(1,2-epoxypentyl)cyclohexyl]benzonitrile (trans-1,2-epoxypentyl/cis-1,2-epoxypentyl ratio about 5:95) as a colourless oil; Rf-values (ethyl acetate/petroleum ether vol. 10:90): trans-1,2-epoxypentyl isomer 0.17, cis-1,2-epoxypentyl isomer 0.14.

c) A solution of 2.46 g of triphenylphosphine in 30 ml of methylene chloride was placed at 0° C. while gassing with argon in a round flask equipped with a dropping funnel and treated dropwise with an about 1M solution of bromine in methylene chloride until a slight yellow colour persisted. The solution was subsequently concentrated cautiously on a rotary evaporator and the residue was dried in a high vacuum. The resulting, crystalline residue was suspended in 30 ml of benzene, the suspension was treated with a solution of 2.1 g of p-[trans-4-(1,2-epoxypentyl)cyclohexyl]benzonitrile in 10 ml of benzene and the mixture was heated to reflux for 3 hours. Filtration of the warm reaction solution on silica gel with toluene gave 3.0 g of a crystalline crude product which, after low-pressure chromatography (0.5 bar) on silica gel with hexane/toluene (vol. 1:1) yielded 2.61 g (81%) of almost pure p-[trans-4-(erythro-1,2-dibromopentyl)cyclohexyl]benzonitrile as colourless crystals. By recrystallization from 90 ml of petroleum ether/ethyl acetate (vol. 2:1) there were finally obtained 2.09 g (65%) of very pure erythro dibromide; m.p. 140.9° C.

d) A mixture of 2.75 g of p-[trans-4-(erythro-1,2-dibromopentyl)cyclohexyl]benzonitrile and 20 ml of glacial acetic acid was treated with 2.42 g of zinc powder at room temperature while gassing with argon in a sulphonation flask equipped with a mechanical stirrer and a thermometer and the mixture was then stirred for 2 hours, whereby the reaction mixture warmed to 33° C. and the educt gradually passed into solution. The reaction mixture was subsequently poured into 100 ml of water and extracted three times with 100 ml of petroleum ether each time. The organic phases were washed twice with 100 ml of water each time and once with 50 ml of saturated sodium hydrogen carbonate solution, dried over magnesium sulphate and concentrated. There were thus obtained 1.43 g (99%) of p-[trans-4-(1E-pentenyl)cyclohexyl]benzonitrile in a purity of 99.5%; m.p. (C-N) 15.6° C., cl.p. (N-I) 58.5° C.

The following compounds were manufactured in an analogous manner:

p-[trans-4-(1E-Propenyl)cyclohexyl]benzonitrile; m.p. (C-N) 66.3° C., cl.p. (N-I) 73.0° C.,
p-[trans-4-(1E-butenyl)cyclohexyl]benzonitrile; m.p. (C-N) 45.1° C., cl.p. (N-I) 51.8° C.,
p-[trans-4-(1E-hexenyl)cyclohexyl]benzonitrile; m.p. (C-N) 14.4° C., cl.p. (N-I) 39.2° C.,
p-[trans-4-(1E-heptenyl)cyclohexyl]benzonitrile; m.p. (C-N) 17.9° C., cl.p. (N-I) 49.2° C.,
p-[trans-4-(3E-pentenyl)cyclohexyl]benzonitrile; m.p. (C-N) 59.8° C., cl.p. 73.7° C.,
p-[trans-4-(3E-hexenyl)cyclohexyl]benzonitrile; m.p. (C-N) 31.1° C., cl.p. (N-I) 50.2° C.,
p-[trans-4-(3E-heptenyl)cyclohexyl]benzonitrile; m.p. (C-N) 15.4° C., cl.p. (N-I) 48.3° C.,
4'-(3E-pentenyl)-4-biphenylcarbonitrile; m.p. (C-I) 76.8° C., cl.p. (N-I) 72.6° C.,
4'-[trans-4-(1E-pentenyl)cyclohexyl]-4-biphenylcarbonitrile; m.p. (C-N) 125.9° C., cl.p. (N-I) 253.5° C.,
4'-[trans-4-(3E-pentenyl)cyclohexyl]-4-biphenylcarbonitrile; m.p. (C-N) 124.1° C., cl.p. 242.6° C.,
4-(3E-pentenyl)cyclohexanecarbonitrile.

EXAMPLE 9

A mixture of 3.79 g of p-[trans-4-(1-hexenyl)cyclohexyl]benzonitrile (prepared in accordance with Example 8a; 1E-hexenyl/1Z-hexenyl ratio about 5:95) and 758 mg of benzenesulphinic acid in 50 ml of 1,4-dioxan was boiled under reflux for 15 hours while gassing with argon in a round flask equipped with a magnetic stirrer and a reflux condenser. Subsequently, a further 379 mg of benzenesulphinic acid were added and the mixture was heated to reflux for a further 4 hours. The cooled reaction mixture was then poured into 50 ml of 1N sodium hydroxide solution and extracted three times with 100 ml of hexane each time. The organic phases were washed twice with 50 ml of water each time, dried over magnesium sulphate and concentrated. Three-fold crystallization of the quantitatively recovered, equilibrated olefin mixture (1E-hexenyl/1Z-hexenyl ratio 80.4:19.6) from methanol finally gave 1.74 g (46%) of p-[trans-4-(1E-hexenyl)cyclohexyl]benzonitrile (containing 0.3% 1Z-hexenyl isomer) with m.p. (C-N) 14.3° C. and cl.p. (N-I) 39.5° C. The mother liquors were not worked-up. If desired, these can, however, again be equilibrated and crystallized.

All nitriles manufactured in Example 8 can be obtained in an analogous manner.

EXAMPLE 10 a) A suspension of 5.1 g of propyl-triphenylphosphonium bromide in 80 ml of t-butyl methyl ether was treated within 5 minutes with 1.48 g of potassium t-butylate while gassing with argon at −10° C. and the mixture was stirred at room temperature for a further 60 minutes. Thereafter, the mixture was treated with 5 minutes at 0° C. with a solution of 2.0 g of [trans-4-(p-cyanophenyl)cyclohexyl]acetaldehyde in 25 ml of t-butyl methyl ether and the resulting mixture was stirred for a further 45 minutes at room temperature. The reaction mixture was subsequently poured into 100 ml of water and extracted three times with 100 ml of diethyl ether each time. The organic phases were washed twice with 100 ml of water each time, dried over magnesium sulphate and concentrated. The residue was dissolved in 20 ml of ethyl acetate and the solution was treated with 250 ml of petroleum ether. After leaving to stand for 10 minutes at −20° C. the precipitated triphenylphosphine oxide was filtered off and the filtrate was concentrated to dryness. Low-pressure chromatography (0.5 bar) of the yellowish, oily residue (3.33 g) on silica gel with ethyl acetate/petroleum ether (vol. 3:97) gave 2.1 g of p-[trans-4-(2-pentenyl)cyclohexyl]benzonitrile as a colourless oil containing 92.7% of p-[trans-2-(2Z-pentenyl)cyclohexyl]benzonitrile and 6.6% of p-[trans-4-(2E-pentenyl)cyclohexyl]benzonitrile. The material was reacted further without additional purification. If desired, however, this mixture of isomers can be separated by chromatography on silica gel coated with silver nitrate (as illustrated in paragraph d).

b) A solution of 1.59 g of 90 percent m-chloroperbenzoic acid in 60 ml of methylene chloride was treated with 4.0 g of ground potassium carbonate. The suspension obtained was treated dropwise within 5 minutes at 0° C. with a solution of 2.1 g of p-[trans-4-(2-pentenyl)cyclohexyl]benzonitrile (containing 92.7% 2Z-isomer and 6.6% 2E-isomer) in 20 ml of methylene chloride and the mixture was then stirred for a further 3 hours at room temperature, whereby a further 0.8 g of m-chloroperbenzoic acid was added after 1 hour and after 2 hours. The reaction mixture was subsequently poured into 150 ml of 10 percent sodium thiosulphate solution and extracted three times with 100 ml of methylene chloride each time. The organic phases were washed with 100 ml of 10 percent sodium thiosulphate solution and with 100 ml of saturated sodium carbonate solution, dried over magnesium sulphate and concentrated. This gave 2.2 g (99%) of p-[trans-4-(2,3-epoxypentyl)cyclohexyl]benzonitrile as colourless crystals; Rf-value (ethyl acetate/petroleum ether vol. 10:90) 0.15. This material was processed without additional purification.

c) A solution 2.6 g of triphenylphosphine in 30 ml of methylene chloride was treated dropwise at 0° C. with a solution of 0.519 ml of bromine in 20 ml of methylene chloride until a slight yellow colour persisted. The yellow suspension obtained was cautiously concentrated to dryness on a rotary evaporator and the yellowish, crystalline residue was dried in a high vacuum (0.5 Torr) at room temperature for 1 hour. The triphenylphosphine-bromine obtained was suspended in 50 ml of toluene and the suspension was concentrated to dryness on a rotary evaporator. Thereafter, the residue was suspended in 30 ml of toluene, the suspension was treated with a solution of 2.2 g of p-[trans-4-(2,3-epoxypentyl)cyclohexyl]benzonitrile in 10 ml of toluene and the mixture was stirred for 2 hours at 80° C. bath temperature. Low-pressure chromatography (0.5 bar) of the cooled reaction mixture on silica gel with toluene gave 2.83 g (84%) of p-[trans-4-(2,3-dibromopentyl)cyclohexyl]benzonitrile as a yellowish oil (containing 66.6% erythro form and 32.8% threo form); Rf-value (ethyl acetate/petroleum ether vol. 10:90) 0.33. This material was processed without additional purification.

d) A solution of 1.98 g of p-[trans-4-(2,3-dibromopentyl)cyclohexyl]benzonitrile (erythro/threo 66.6:32.8) in 30 ml of glacial acetic acid was treated at room temperature with 2.0 g of zinc powder while gassing with argon and the suspension was stirred at room temperature for 1 hour. The reaction mixture was subsequently poured into 100 ml of water and extracted three times with 100 ml of petroleum ether each time. The organic phases were washed twice with 100 ml of water each time, dried over magnesium sulphate and concentrated. Low-pressure chromatography (0.5 bar) of the yellowish residue on silver nitrate-coated silica gel with hexane/diethyl ether (vol. 90:10) gave 586 mg (48%) of p-[trans-4-(2E-pentenyl)cyclohexyl]benzonitrile and 171 mg (14%) of p-[trans-4-(2Z-pentenyl)cyclohexyl]benzonitrile as colourless oils. The 2E-isomer has a melting point of 9.6° C. and 16.1° C. (2 modifications) and a virtual clearing point of −67° C.; the 2Z-isomer has a melting point of −7.7° C. and a virtual clearing point of −54° C.

The coating of silica gel or thin-layer plates with silver nitrate was carried out as follows;

34 g of silver nitrate were dissolved in 1000 ml of acetonitrile. The thin-layer plates were dipped once for a short time in the silver nitrate solution and were thereafter dried for 2 hours at 80° C. in vacuo (12 Torr). 300 g of silica gel were then added to the remaining silver nitrate solution, mixed well, cautiously concentrated to dryness on a rotary evaporator and dried at room temperature in a high vacuum (0.5 Torr) for 2 hours.

EXAMPLE 11 a) 149 g of methoxymethyl-triphenylphosphonium chloride and 860 ml of t-butyl methyl ether were placed at room temperature in a sulphonation flask while stirring and gassing with nitrogen, the suspension was cooled to −10° C. and treated with 51.6 g of potassium t-butylate within 10 minutes. The suspension was stirred for a further 30 minutes at −10° C. to 0° C. and then treated dropwise within 45 minutes at 0° C. with a solution of 47.3 g of 4,4-ethylenedioxycyclohexanone in 720 ml of tetrahydrofuran. The orange suspension was stirred for a further 2 hours at room temperature, then poured into 5 l of hexane, stirred for 10 minutes and suction filtered. The filtrate was concentrated in vacuo and the yellow-brownish oil obtained (104.1 g) was treated with 500 ml of hexane and suction filtered. The filtrate was concentrated in vacuo, whereby 61.7 g of yellow-brownish oil were obtained. Chromatographic separation of this crude product on silica gel with methylene chloride/acetone (vol. 98:2 and 95:5) finally gave 53.5 g of 1,1-ethylenedioxy-4-(methoxymethylene)cyclohexane as a colourless oil.

b) A mixture of 28.2 g of 1,1-ethylenedioxy-4-(methoxymethylene)cyclohexane, 770 ml of glacial acetic acid and 385 ml of water was heated to reflux for 1 hour in a round flask while gassing with nitrogen. Thereafter, the yellowish clear solution was cooled to room temperature, diluted with 800 ml of water and extracted three times with 700 ml of methylene chloride each time. The organic phases were washed twice with 500 ml of 10 percent (wt./vol.) sodium carbonate solution each time, dried over sodium sulphate, filtered and concentrated. Chromatographic separation of the brownish liquid obtained (18.5 g) on silica gel with methylene chloride as the eluent finally gave 16.7 g of 4-formylcyclohexanone as a brownish liquid.

c) 63.3 g of p-cyanobenzyl-triphenylphosphonium chloride, 17.2 g of potassium t-butylate and 195 ml of ethylene glycol dimethyl ether were placed in a sulphonation flask while stirring and gassing with nitrogen, whereby the internal temperature rose to 44° C. The brown suspension was cooled to 0° C. and treated within 2 minutes with a solution of 16.7 g of 4-formylcyclohexanone in 100 ml of ethylene glycol dimethyl ether. Thereafter, the cooling bath was removed and the reaction mixture was stirred for a further 3.5 hours at room temperature. The suspension was subsequently poured into 500 ml of water and extracted three times with 600 ml of methylene chloride each time. The organic phases were washed twice with 500 ml of 10 percent (wt./vol.) sodium chloride solution each time, dried over sodium sulphate, filtered and concentrated, whereby 76.9 g of a brownish paste remained behind. Chromatographic separation of this crude product on silica gel with methylene chloride as the eluent gave 33.0 g of 4-[2-(p-cyanophenyl)vinyl]cyclohexanone as a yellow-brownish oil.

d) A mixture of 33.0 g of 4-[2-(p-cyanophenyl)vinyl]cyclohexanone, 520 ml of toluene, 260 ml of ethanol and 3.2 g of 5 percent palladium/carbon was placed at room temperature in a round flask equipped with a magnetic stirrer and the mixture was hydrogenated until the hydrogen uptake had come to a standstill. The black suspension was subsequently suction filtered (rinsing with toluene) and the filtrate was concentrated in vacuo. The slightly turbid, yellowish oil obtained (34.1 g) was separated by chromatography on silica gel. Methylene chloride/hexane (vol. 1:1), methylene chloride/hexane (vol. 8:2) and methylene chloride eluted 25.6 g of yellowish oil which was crystallized from t-butyl methyl ether. There were thus obtained 22.6 g of 4-[2-(p-cyanophenyl)ethyl]cyclohexanone as colourless crystals with m.p. 62.5°–64.3° C.

e) 4-[2-(p-Cyanophenyl)ethyl]cyclohexanone was converted into the following compounds in an analogous manner to Examples 5 and 8:

p-[2-(trans-4-(1E-Propenyl)cyclohexyl)ethyl]benzonitrile; m.p. (C-I) 61.3° C., cl.p. (N-I) 54.2° C.,
p-[2-(trans-4-(1E-butenyl)cyclohexyl)ethyl]benzonitrile; m.p. (C-I) 42.6° C., cl.p. (N-I) 39.7° C.,
p-[2-(trans-4-(1E-pentenyl)cyclohexyl)ethyl]benzonitrile; m.p. (C-N) 25.1° C., cl.p. (N-I) 47.5° C.,
p-[2-(trans-4-(1E-hexenyl)cyclohexyl)ethyl]benzonitrile; m.p. (C-N) 16.8° C. and 19.7° C. (2 modifications), cl.p. (N-I) 34.6° C.,
p-[2-(trans-4-(1E-heptenyl)cyclohexyl)ethyl]benzonitrile; m.p. (C-N) 31.6° C., cl.p. (N-I) 43.6° C.

EXAMPLE 12

1.1 g of p-[trans-4-(1E-pentenyl)cyclohexyl]benzonitrile were boiled at 180° C. for 16 hours while gassing with argon in 17.5 ml of a 10 percent solution of potassium hydroxide in diethylene glycol. After cooling to room temperature the dark brown reaction mixture was diluted with 20 ml of water, made acid with 25 percent hydrochloric acid and extracted four times with 100 ml of ethylene chloride each time. The organic phases were washed twice with 80 ml of water each time, dried over magnesium suphate and active carbon and concentrated. There were obtained 1.16 g (98%) of p-[trans-4-(1E-pentenyl)cyclohexyl]benzoic acid as beige crystals; Rf-value (toluene/ethyl acetate vol. 3:1) 0.45.

The following compounds were prepared in an analogous manner:
trans-4-(3-Butenyl)cyclohexanecarboxylic acid,
trans-4-(3E-pentenyl)cyclohexanecarboxylic acid,
p-[trans-4-(1E-hexenyl)cyclohexyl]benzoic acid,
p-[trans-4-(3-butenyl)cyclohexyl]benzoic acid,
p-[trans-4-(3E-pentenyl)cyclohexyl]benzoic acid.

EXAMPLE 13 a) 20 ml of a 0.462M solution of methylmagnesium iodide in diethyl ether were treated within 5 minutes with a solution of 1.7 g of p-[trans-4-(erythro-1,2-dibromopentyl)cyclohexyl]benzonitrile in 20 ml of toluene while gassing with argon at 40° C. Thereafter, sufficient diethyl ether was distilled off by warming under a vigorous stream of argon so that the internal temperature rose to 50° C. and then using a reflux condenser the mixture was stirred at this temperature for a further 15 hours. The reaction mixture was subsequently poured on to 100 ml of ice-water and extracted three times with 100 ml of diethyl ether each time. The organic phases were washed twice with 100 ml of water each time, dried over magnesium sulphate and concentrated. Low-pressure chromatography (0.5 bar) of the yellowish, crystalline residue (1.73 g) on silica gel with ethyl acetate/petroleum ether (vol. 10:90) gave 1.31 g (74%) of p-[trans-4-(erythro-1,2-dibromopentyl)cyclohexyl]acetophenone as colourless crystals which were reacted further without additional purification; Rf-value (ethyl acetate/petroleum ether vol. 10:90) 0.26.

b) A solution of 817 mg of p-[trans-4-(erythro-1,2-dibromopentyl)cyclohexyl]acetophenone in 40 ml of methylene chloride was treated at room temperature while gassing with argon with 233 mg of sodium hydrogen carbonate and 392 mg of 90 percent m-chloroperbenzoic acid and the mixture was stirred, whereby in each case at intervals of 2.5 hours a further 233 mg of sodium hydrogen carbonate and 392 mg of 90 percent m-chloroperbenzoic acid were added. After stirring and carrying out the additions for a total of 70 hours the reaction mixture was poured into 80 ml of 10 percent sodium thiosulphate solution and extracted three times with 60 ml of methylene chloride each time. The organic phases were washed twice with 60 ml of 10 percent sodium thiosulphate solution each time, dried over magnesium sulphate and concentrated. Low pressure chromatography (0.5 bar) of the yellowish, crystalline residue (0.98 g) on silica gel with ethyl acetate/petroleum ether (vol. 5:95) gave 0.71 g (84%) of p-[trans-4-(erythro-1,2-dibromopentyl)cyclohexyl]phenyl acetate as yellowish crystals which were reacted further without additional purification; Rf-value (ethyl acetate/petroleum ether vol. 10:90) 0.28.

c) A solution of 710 mg of p-[trans-4-(erythro-1,2-dibromopentyl)cyclohexyl]phenyl acetate in 40 ml of glacial acetic acid was treated with 676 mg of zinc powder at room temperture while gassing with argon. The grey suspension was stirred for 2 hours at room temperature, then poured into 100 ml of water and extracted three times with 80 ml of petroleum ether each time. The organic phases were washed twice with 80 ml of water each time, dried over magnesium sulphate and concentrated. There were obtained 385 mg (85%) of p-[trans-4-(1E-pentenyl)cyclohexyl]phenyl acetate as colourless crystals. Rf-value (ethyl acetate/petroleum ether vol. 10:90) 0.35.

d) 385 mg of p-[trans-4-(1E-pentenyl)cyclohexyl]phenyl acetate were dissolved in 100 ml of a 1N solution of potassium hydroxide in methanol while gassing with argon and the mixture was stirred at room temperature for 30 minutes. Subsequently, the reaction mixture was poured into 80 ml of 1N hydrochloric acid and extracted three times with 60 ml of diethyl ether each time. The organic phases were washed twice with 60 ml of water each time, dried over magnesium sulphate and concentrated. There were obtained 328 mg (100%) of p-[trans-4-(1E-pentenyl)cyclohexyl]phenol as colourless crystals; Rf-value (ethyl acetate/petroleum ether vol. 10:90) 0.17.

The following compounds were prepared in an analogous manner:
p-[trans-4-(1E-Propenyl)cyclohexyl]phenol,
p-[2-(trans-4-(1E-pentenyl)cyclohexyl)ethyl]phenol.

EXAMPLE 14 a) A solution of methylmagnesium iodide in diethyl ether (prepared from 384 mg of magnesium shavings and 0.984 ml of methyl iodide in 30 ml of diethyl ether) was treated dropwise at room temperature with a solution of 2.0 g of p-[trans-4-(1E-pentenyl)cyclohexyl]benzonitrile. The mixture was heated to reflux for 15 minutes. Subsequently, 30 ml of toluene were added to the reaction mixture, the diethyl ether was distilled off and the mixture was heated to reflux for a further 1.5 hours. Thereafter, the reaction mixture was treated cautiously at 0° C. with saturated ammonium chloride solution and partitioned three times in diethyl ether/water. The organic extracts were washed twice with water, dried over magnesium sulphate, filtered and evaporated. Chromatographic separation of the yellow crystalline residue (2.6 g) on silica gel with ethyl acetate/petroleum ether (vol. 5:95) gave 1.85 g (87%) of p-[trans-4-(1E-pentenyl)cyclohexyl]acetophenone as light yellow crystals; m.p. 51.2° C.

b) A solution of 2.63 g of p-[trans-4-(1E-pentenyl)cyclohexyl]acetophenone in 90 ml of methylene chloride was treated in succession with 7.46 g of m-chloroperbenzoic acid and 100 mg of 2,6-di-t-butyl-p-cresol at 0° C. while gassing with argon. The mixture was stirred at room temperature for 40 hours with the exclusion of light. Subsequently, the reaction mixture was partitioned in methylene chloride/10 percent sodium thiosulphate solution and the organic phase was washed once with 10 percent sodium thiosulphate solution and twice with sodium hydrogen carbonate solution. The aqueous phases were back-extracted three times with methylene chloride. The combined organic phases were dried over magnesium sulphate, filtered and evaporated. The yellow, oily residue of 4-acetoxy-1-[trans-4-(1,2-epoxypentyl)cyclohexyl]benzene was dissolved in 100 ml of 1N methanolic potassium hydroxide solution and the resulting solution was stirred for 1 hour at room temperature. The mixture was subsequently adjusted to about pH 8 with 10 ml of 10 percent hydrochloric acid and partitioned in diethyl ether/water. The aqueous phase was extracted three times with diethyl ether. The organic phases were dried over magnesium sulphate, filtered and evaporated. Chromatographic separation of the residual brown oil (2.96 g) on silica gel with ethyl acetate/petroleum ether (vol. 10:90) gave 2.16 g of p-[trans-4-(1,2-epoxypentyl)cyclohexyl]phenol as yellowish crystals.

EXAMPLE 15

A mixture of 200 mg of trans-4-(1E-butenyl)cyclohexanecarboxylic acid, 272.4 mg of dicyclohexylcarbodimide, 13.4 mg of 4-(dimethylamino)pyridine, 169.7 mg of trans-4-(1E-butenyl)cyclohexanol and 4 ml of methylene chloride was stirred at room temperature for 21 hours while gassing with argon. Subsequently, the heterogeneous reaction mixture was diluted with 10 ml of hexane and filtered (rinsing with hexane). The concentrated filtrate was taken up in 30 ml of hexane and the solution was washed in each case once with 30 ml of 5 percent hydrochloric acid, 30 ml of saturated sodium hydrogen carbonate solution and 30 ml of saturated sodium chloride solution, dried over magnesium sulphate and concentrated. Low-pressure chromatography (0.5 bar) of the colourless oil (450 mg) on silica gel with ethyl acetate/petroleum ether (vol. 1:99) gave 280 mg (80.1%) of trans-4-(1E-butenyl)cyclohexanecarboxylic acid trans-4-(1E-butenyl)cyclohexyl ester as colourless crystals. Recrystallization from 15 ml of methanol at −20° C. gave 223 mg of ester as colourless needles with melting point (C-N) 46.3° C. and cl.p. (N-I) 58.7° C.

The following compounds were manufactured in an analogous manner:
trans-4-(1E-Butenyl)cyclohexanecarboxylic acid trans-4-(1E-pentenyl)cyclohexyl ester; m.p. (C-S) 28.8° C., transition S-N 61.5° C., cl.p. (N-I) 67.5° C.,
trans-4-(1E-pentenyl)cyclohexanecarboxylic acid trans-4-(1E-butenyl)cyclohexyl ester; m.p. (C-S) 30.5° C., transition S-N 55.2° C., cl.p. (N-I) 68.0° C.,
trans-4-(1E-pentenyl)cyclohexanecarboxylic acid trans-4-(1E-pentenyl)cyclohexyl ester; m.p. (C-S) 39.6° C., transition S-N 75.4° C., cl.p. (N-I) 77.1° C.,
trans-4-(3-butenyl)cyclohexanecarboxylic acid trans-4-(1E-butenyl)cyclohexyl ester; m.p. (C-S) 26.4° C., transition S-N 30.7° C., cl.p. (N-I) 43.3° C.,
trans-4-(3E-pentenyl)cyclohexanecarboxylic acid trans-4-(1E-butenyl)cyclohexyl ester; m.p. (C-S) 25.7° C., transition S-N 31.8° C., cl.p. (N-I) 70.0° C.,
trans-4-(3E-pentenyl)cyclohexanecarboxylic acid p-[trans-4-(1E-pentenyl)cyclohexyl]phenyl ester; m.p. (C-S) 55.0° C., transition S-N 166.5° C., cl.p. (N-I) 221.5° C.,
trans-4-(4-pentenyl)cyclohexanecarboxylic acid p-(4-pentenyl)phenyl ester,
trans-4-pentylcyclohexanecarboxylic acid p-allyloxyphenyl ester; m.p. (C-N) 33.7° C., cl.p. (N-I) 77.9° C., trans-4-(4-pentenyl)cyclohexanecarboxylic acid p-allyloxyphenyl ester; m.p. (C-N) 32.2° C., cl.p. (N-I) 51.8° C., p-[trans-4-(3E-pentenyl)cyclohexyl]benzoic acid p-(3E-pentenyl)phenyl ester; m.p. (C-S) 93.5° C., transition S-S 95° C., transition S-N 125° C., cl.p. (N-I) 205° C.

EXAMPLE 16

A mixture of 400 mg of p-(trans-4-pentylcyclohexyl)phenol, 853 mg of ground potassium carbonate, 0.5 ml of allyl bromide and 50 ml of acetone was stirred at room temperature overnight while gassing with argon. Subsequently, the heterogeneous reaction mixture was filtered (rinsing with hexane) and the filtrate was concentrated. The residue was taken up in 50 ml of hexane and the solution was washed twice with 50 ml of water each time, dried over magnesium sulphate and concentrated. Low-pressure chromatography (0.5 bar) of the oily residue (490 mg) on silica gel with hexane/diethyl ether (vol. 90:10) gave 435 mg (93.5%) of product as colourless crystals in a purity of 95%. Recrystallization from methanol at 0° C. gave 155 mg of 4-allyloxy-1-(trans-4-pentylcyclohexyl)benzene as colourless crystals in a purity of 99.8%; m.p. (C-N) 31.9° C., cl.p. (N-I) 40.9° C.

The following compounds can be manufactured in an analogous manner:

4-(3-Butenyl)oxy-1-(trans-4-pentylcyclohexyl)benzene; m.p. (C-I) 29.9° C., virtual cl.p. −5.0° C., 4-(2E-butenyl)oxy-1-(trans-4-pentylcyclohexyl)benzene; m.p. (C-N) 32.0° C. and 38.4° C., cl.p. (N-I) 66.8° C., 4-(2E-butenyl)oxy-1-(trans-4-propylcyclohexyl)benzene; m.p. (C-N) 42.3° C., cl.p. (N-I) 56.5° C., 4-(2E-butenyl)oxy-1-[trans-4-(1E-propenyl)cyclohexyl]benzene; m.p. (C-N) 52.0° C., cl.p. (N-I) 72.8° C., 4-allyloxy-1-[2-(trans-4-pentylcyclohexyl)ethyl]benzene; m.p. (C-$S_B$) 15.7° C., transition $S_B$-N 23.8° C., cl.p. (N-I) 40.7° C., 4-(2E-butenyl)oxy-1-[2-(trans-4-propylcyclohexyl)ethyl]benzene; m.p. (C-N) 44.6° C., cl.p. (N-I) 52.5° C., 4-(3-butenyl)oxy-1-[2-(trans-4-propylcyclohexyl)ethyl]benzene; m.p. (C-S) 6.0° C., transition S-N 16.3° C., cl.p. (N-I) 16.5° C., 4-(3-butenyl)oxy-1-[2-(trans-4-pentylcyclohexyl)ethyl]benzene; m.p. (C-$S_B$) 1.6° C. and 5.0° C. (2 modifications), cl.p. ($S_B$-I) 33° C., 4-(4-pentenyl)oxy-1-[2-(trans-4-propylcyclohexyl)ethyl]benzene; m.p. (C-I) 32.1° C., cl.p. (N-I) 29.6° C., 4-(4-pentenyl)oxy-1-[2-(trans-4-pentylcyclohexyl)ethyl]benzene; m.p. (C-$S_B$) 29.7° C., cl.p. ($S_B$-I) 42.3° C., 4-allyloxy-2-fluoro-1-[2-(trans-4-pentylcyclohexyl)ethyl]benzene; m.p. (C-N) 17.2° C., cl.p. 20.2° C., 4-(3-butenyloxy)-2-fluoro-1-[2-(trans-4-pentylcyclohexyl)ethyl]benzene; m.p. (C-I) 10.8° C., cl.p. (N-I) 4.7° C., 4-(4-pentenyl)oxy-2-fluoro-1-[2-(trans-4-pentylcyclohexyl)ethyl]benzene; m.p. (C-I) 28.2° C., cl.p. (N-I) 20.0° C., 4-(5-hexenyl)oxy-2-fluoro-1-[2-(trans-4-pentylcyclohexyl)ethyl]benzene; m.p. (C-N) 11.5° C., cl.p. (N-I) 12.7° C., 2-(p-allyloxyphenyl)-5-butylpyrimidine; m.p. (C-I) 56° C., 2-[p-(3-butenyl)oxyphenyl]-5-butylpyrimidine; m.p. (C-I) 37.3° C., cl.p. (N-I) 12.5° C., 2-[p-(4-pentenyl)oxyphenyl]-5-butylpyrimidine; m.p. (C-I) 36.5° C., cl.p. (N-I) 35.9° C.

EXAMPLE 17

A solution of 16.1 g of diethyl 2-(1E-pentenyl)malonate (Tetrahedron Lett. 1979, 861) in 75 ml of tetrahydrofuran was added dropwise within 1 hour at 5° C. to a suspension of 5.3 g of lithium aluminium hydride in 200 ml of dry tetrahydrofuran while stirring in an inert gas atmosphere. The mixture was stirred for a further 3.5 hours at room temperature and then treated dropwise successively with 15 ml of acetone and 20 ml of saturated sodium hydrogen carbonate solution. The reaction mixture was filtered, the filtrate was concentrated and the residue (8.2 g) was distilled in a bulb-tube at 150° C./about 1 Torr. There were thus obtained 6.5 g of 2-(1E-pentenyl)-1,3-propanediol as a colourless oil.

The following compounds were prepared in an analogous manner:

2-(1E-Propenyl)-1,3-propanediol,
2-(1E-butenyl)-1,3-propanediol,
2-(1E-hexenyl)-1,3-propanediol,
2-(1E-heptenyl)-1,3-propanediol.

EXAMPLE 18 a) 7.05 g of sodium were dissolved in a solution of 49 g of diethyl malonate in 175 ml of ethanol. The still warm solution (50° C.) was treated dropwise within 15 minutes with 45.6 g of 5-bromo-1-pentene and the mixture was heated to boiling for 2 hours. After cooling the reaction mixture was poured into 500 ml of diethyl ether and 300 ml of semi-saturated sodium chloride solution. The aqueous phase was separated and back-extracted twice with 200 ml of diethyl ether each time. The organic phases were washed twice with 150 ml of semi-saturated sodium chloride solution each time, dried over sodium sulphate, filtered and concentrated. Chromatographic separation of the resulting, yellow liquid (55.2 g) on silica gel with hexane/ethyl acetate (vol. 95:5) gave 33.2 g of diethyl (4-pentenyl)-malonate as a colourless liquid.

b) A suspension of 13.8 g of lithium aluminium hydride in 500 ml of tetrahydrofuran was treated dropwise under nitrogen at 0°-5° C. within 1 hour with a solution of 33.2 g of diethyl (4-pentenyl)malonate in 125 ml of tetrahydrofuran. The mixture was stirred overnight at room temperature and then heated to boiling for 3 hours. After cooling there were cautiously added dropwise to the reaction mixture firstly 25 ml of acetone and then 25 ml of saturated sodium hydrogen carbonate solution. The resulting slurry was suction filtered and the residue on the suction filter was washed four times with tetrahydrofuran. Concentration of the filtrate gave 17.8 g of 2-(4-pentenyl)-1,3-propanediol (purity 89%) as a yellow liquid.

c) A mixture of 3.6 g of 2-(4-pentenyl)-1,3-propanediol, 4,4 of p-(3-butenyl)oxybenzaldehyde, 75 ml of toluene and 3 drops of 10 percent sulphuric acid is heated to boiling for 2.5 hours, whereby about 50 ml of wet solvent are distilled off and are replaced by the dropwise addition of 50 ml of fresh toluene. Thereafter, the mixture is neutralized with 4 drops of triethylamine and, after cooling, is washed with 5 percent sodium hydrogen carbonate solution and water. The organic phase is dried over sodium sulphate and concentrated. Chromatographic separation of the residue on silica gel with hexane/ethyl acetate and recrystallization from hexane gives trans-2-[p-(3-butenyl)oxyphenyl]-5-(4-pentenyl)-m-dioxane with m.p. (C-I) 17.8° C. and cl.p. (N-I) 7.3° C.

The following compounds can be manufactured in an analogous manner:

trans-2-(p-Allyloxyphenyl)-5-pentyl-m-dioxane; m.p. (C-N) 41.6° C., cl.p. (N-I) 42.5° C., trans-2-[p-(3-butenyl)oxyphenyl]-5-pentyl-m-dioxane; m.p. (C-N) 31.4° C. cl.p. (N-I) 35.2° C.

EXAMPLE 19 a) A suspension of 829 mg of sodium borohydride in 20 ml of methanol/diethyl ether (vol. 9:1) was treated dropwise within 5 minutes at 0° C. with a solution of 3.0 g of trans-4-cyanocyclohexanecarboxyaldehyde in 30 ml of methanol/diethyl ether (vol. 9:1). The reaction mixture was stirred for a further 2 hours at 10° C., then treated with 10 ml of dilute hydrochloric acid and partitioned in methylene chloride/water. The aqueous phase was extracted three times with methylene chloride. The organic phases were washed twice with water, dried over magnesium sulphate, filtered and concentrated. There were obtained 3.0 g (98%) of trans-4-(hydroxymethyl)cyclohexanecarbonitrile as a colourless oil.

b) A solution of 3.0 g of trans-4-(hydroxymethyl)cyclohexanecarbonitrile in 10 ml of pyridine was treated dropwise within 3 minutes at 0° C. with a solution of 6.81 g of p-tosyl chloride in 10 ml of pyridine. The reaction mixture was stirred for 15 hours at room temperature, then made acid (pH about 2) with 50 ml of 25% hydrochloric acid and partitioned in chloroform/water. The aqueous phase was extracted three times with chloroform. The organic phases were washed twice with water, dried over magnesium sulphate, filtered and concentrated. There were obtained 6.3 g (99%) of trans-4-(p-tosyloxymethyl)cyclohexanecarbonitrile as colourless crystals.

c) A solution of 6.3 g of trans-4-(p-tosyloxymethyl)cyclohexanecarbonitrile in 80 ml of acetone was treated with 3.87 g of sodium iodide and the mixture was heated to reflux while stirring for 15 hours. Thereafter, the white suspension was filtered and the filtrated was concentrated. The residue was partitioned in water/chloroform. The aqueous phase was extracted three times with chloroform. The organic phases were washed twice with water, dried over magnesium sulphate, filtered and concentrated. There were obtained 4.8 g (89%) of trans-4-(iodomethyl)cyclohexanecarbonitrile as a yellowish oil.

d) A suspension of 9.14 g of copper(I) iodide in 90 ml of tetrahydrofuran was treated within 5 minutes at 78° C. with 25.7 ml of 1.5M solution of methyl lithium in tetrahydrofuran using a syringe. The suspension was stirred for a further 45 minutes at −78° C., then left to warm to 0° C. and stirred for a further 3 minutes at 0° C. Thereafter, the suspension was again cooled to −78° C. and treated within 5 minutes using a steel cannula with a Grignard solution prepared from 4.56 ml of 4-bromo-1-butene and 1.1 g of magnesium in 60 ml of tetrahydrofuran. The suspension was stirred for a further 20 minutes at −78° C., then left to warm to 15° C. and stirred for a further 5 minutes at 15° C. Thereafter, the solution was again cooled to −78° C. and treated dropwise within 5 minutes with a solution of 4.8 g of trans-4-(iodomethyl)cyclohexanecarbonitrile in 30 ml of tetrahydrofuran. Thereafter, the reaction mixture was left to warm and was stirred for a further 30 minutes at 16° C. Subsequently, the reaction mixture was treated cautiously in a cooling bath with about 50 ml of ammonium chloride solution and partitioned in methylene chloride/ammonium chloride solution. The aqueous phase was extracted three times with methylene chloride. The organic phases were washed once with ammonium chloride solution and twice with water, dried over magnesium sulphate, filtered and concentrated. Chromatographic separation of the yellow, oily residue (3.4 g) on silica gel with ethyl acetate/petroleum ether (vol. 5:95) gave 2.9 g (85%) of trans-4-(4-pentenyl)cyclohexanecarbonitrile as a light yellow oil.

e) A solution of 2.9 g of trans-4-(4-pentenyl)cyclohexanecarbonitrile in 80 ml of diethylene glycol was treated with 8.0 g of potassium hydroxide and the mixture was stirred for 3.5 hours at a bath temperature of 180° C. Subsequently, the reaction mixture was treated with ice, made acid with 25 ml of 25 percent hydrochloric acid and partitioned in methylene chloride/water. The aqueous phase was extracted three times with methylene chloride. The organic phases were washed twice with water, dried over magnesium sulphate, filtered and concentrated. Chromatographic separation of the brown, oily residue (3.5 g) on silica gel with ethyl acetate/petroleum ether (vol. 10:90) gave 2.9 g (90%) of trans-4-(4-pentenyl)cyclohexanecarboxylic acid as a yellowish oil.

EXAMPLE 20 a) A solution of 400 mg of p-(3-hydroxypropyl)-phenol and 0.421 ml of triethylamine in 2.6 ml of methylene chloride was treated portionwise at 0° C. with 539 mg of p-tosyl chloride and the mixture was stirred for a further 5 minutes at 0° C. and for 15 minutes at −5° C. Subsequently, the reaction mixture was diluted with water, made slightly acid with dilute hydrochloric acid and extracted three times with methylene chloride. The organic phases were washed twice with water, dried over magnesium sulphate and freed from solvent. The residual, colourless oil (870 mg) was purified by chromatography on silica gel with ethyl acetate/petroleum ether, whereby 693 mg (83%) of p-(3-hydroxypropyl)-phenyl p-tosylate were isolated as a milky oil.

b) A solution of 12 ml of oxalyl chloride in 380 ml of methylene chloride was treated dropwise at −60° C. with a solution of 19.8 ml of dimethyl sulphoxide in 30 ml of methylene chloride and the mixture was stirred for a further 5 minutes at −60° C. Subsequently, the mixture was treated dropwise with a solution of 38.9 g of p-(3-hydroxypropyl)phenyl p-tosylate in 100 ml of methylene chloride, the resulting mixture was stirred for a further 20 minutes at −60° C. and then treated with 88.5 ml of triethylamine. The reaction mixture was stirred for a further 5 minutes at −60° C., then left to warm slowly to room temperature and stirred for a further 5 minutes at 24° C. The reaction mixture was subsequently treated with water. The organic phases was washed with water and sodium chloride solution (back-extraction with methylene chloride), dried over sodium sulphate and evaporated. Chromatographic separation of the residual, brown-yellow oil (38 g) on silica gel with ethyl acetate/petroleum ether (vol. 40:60) gave 33.8 g of 3-[p-(p-tosyloxy)phenyl]propionaldehyde as a pale yellow oil.

c) A suspension of 14.87 g of methoxymethyl-triphenylphosphonium chloride in 130 ml of t-butyl methyl ether was treated at −20° C. with 5.2 g of potassium t-butylate and the mixture was stirred without cooling for a further 1.2 hours. Subsequently, the mixture was treated dropwise at −5° C. with a solution of 8.8 g of 3-[p-(p-tosyloxy)phenyl]propionaldehyde in 30 ml of tetrahydrofuran. The cooling bath was removed and the mixture was stirred for a further 10 minutes at room temperature. The reaction mixture was then treated with water and partitioned twice in water/diethyl ether. The aqueous phases were back-extracted with diethyl ether. The organic phases were dried over magnesium sulphate and evaporated. The oily residue was dissolved in ethyl acetate and the solution was treated with petroleum ether and freed from precipitated triphenylphosphine oxide by filtration. After evaporation of the filtrate and chromatographic separation of the residue on silica gel there were obtained 4.4 g (44%) of p-(4-methoxy-3-butenyl)phenyl p-tosylate as a slightly yellowish oil.

d) A mixture of 4.3 g of p-(4-methoxy-3-butenyl)phenyl p-tosylate, 60 ml of glacial acetic acid and 30 ml of water was stirred for 40 minutes at 110° C., then cooled to room temperature and diluted with 200 ml of water. The aqueous phase was extracted four times with methylene chloride. The organic phases were washed twice with dilute sodium carbonate solution, dried over magnesium sulphate and freed from solvent. There were obtained 4.35 g of 4-[p-(p-tosyloxy)phenyl]butyraldehyde as a yellowish oil.

e) A suspension of 7.32 g of methyltriphenylphosphonium bromide in 70 ml of t-butyl methyl ether was treated with 2.45 g of potassium t-butylate at −5° C. and the mixture was stirred for a further 40 minutes at room temperature. Subsequently, the mixture was treated slowly at 0° C. with a solution of 4.35 g of 4-[p-(p-tosylosy)phenyl]butyraldehyde in 30 ml of t-butyl methyl ether. The reaction mixture was stirred for a further 5 minutes at 0° C. and for 30 minutes at room temperature, then treated with water and partitioned twice in water/diethyl ether. The aqueous phases were back-extracted with diethyl ether. The organic phases were dried over magnesium sulphate and concentrated. The residue was dissolved in ethyl acetate and the solution was treated with petroleum ether and freed from precipitated triphenylphosphine oxide by filtration. After concentration of the filtrate and chromatographic separation of the residual, yellow oil (4.3 g) on silica gel there were obtained 3.37 g (78%) of p-(4-pentyl)phenyl p-tosylate as a colourless oil.

f) A mixture of 3.35 g of p-(4-pentenyl)phenyl p-tosylate and 50 ml of 10% ethanolic potassium hydroxide solution was stirred for 1 hour at 100° C. Subsequently, the reaction mixture was cooled to room temperature and made acid with dilute hydrochloric acid. The aqueous phase was extracted four times with diethyl ether. The organic phases were washed with water, dried over magnesium sulphate and concentrated. The residual brown oil (1.92 g) was purified by chromatography on silica gel with ethyl acetate/petroleum ether (vol. 8:92), whereby 1.70 g (99%) of p-(4-pentenyl)phenol were obtained as a light yellow oil.

EXAMPLE 21 a) A suspension of 32 g of ethyltriphenylphosphonium bromide in 450 ml of t-butyl methyl ether was treated slowly with 10 g of potassium t-butylate at 0° C. and the mixture was stirred for a further 1 hour without cooling. Subsequently, the mixture was treated slowly at 0° C. with a solution of 15 g of 3-[p-(p-tosyloxy)phenyl]propionaldehyde in 50 ml of tetrahydrofuran and the resulting mixture was then warmed slowly to room temperature. Thereafter, the reaction mixture was treated with water and partitioned twice in diethyl ether/water. The aqueous phases were back-extracted with diethyl ether. The organic phases were dried over magnesium sulphate and concentrated. The oil obtained was freed from triphenylphosphine oxide by repeated dissolution in ethyl acetate, treatment with petroleum ether, filtration and concentration of the filtrate. The yellow oily crude product obtained (18 g) was purified by chromatography on silica gel with petroleum ether and ethyl acetate/petroleum ether. There were obtained 7.1 g (46%) of p-(3-pentenyl)phenyl p-tosylate as a colourless oil (cis/trans mixture).

b) p-(3-Pentenyl)phenyl p-tosylate was oxidized in an analogous manner to Example 8b) with m-chloroperbenzoic acid to p-(3,4-epoxypentyl)phenyl p-tosylate, the epoxide was then converted in an analogous manner to Example 8c) with triphenylphosphine-bromine into p-(erythro-3,4-dibromopentyl)phenyl p-tosylate and finally the dibromide was reduced in an analogous manner to Example 8d) with zinc in glacial acetic acid to p-(3E-pentenyl)phenyl p-tosylate.

c) A mixture of 7.9 g of p-(3E-pentenyl)phenyl p-tosylate and 120 ml of 10% ethanolic potassium hydroxide solution was heated to reflux for 45 minutes, then cooled to room temperature, made acid with hydrochloric acid and partitioned three times in water/diethyl ether. The aqueous phases were back-extracted with diethyl ether. The organic phases were dried over magnesium sulphate and concentrated. The residual oil (4.1 g) was purified by chromatography on silver nitrate-coated silica gel with diethyl ether/hexane. There were obtained 3.15 g (77%) of p-(3E-pentenyl)phenol as a light yellowish liquid.

EXAMPLE 22 a) A suspension of 11.5 g of 3,3-ethylenedioxypropyltriphenylphosphonium bromide in 90 ml of t-butyl methyl ether was treated with 3.02 g of potassium t-butylate at 0° C. and the mixture was then stirred at room temperature for 40 minutes. Thereafter, the mixture was treated dropwise at 5° C. with a solution of 2.6 g of p-cyanobenzaldehyde in 30 ml of tetrahydrofuran and the resulting mixture was stirred for a further 1 hour at room temperature. The reaction mixture was subsequently treated with water. The phases were separated and the aqueous phase was back-extracted twice with tetrahydrofuran. The organic phases were washed twice with water, dried over magnesium sulphate and concentrated. The residue was dissolved in hot ethyl acetate, the solution was treated with petroleum ether and the precipitated triphenylphosphine oxide was filtered off under suction. The yellow oil (4.5 g) obtained after concentrating the filtrate was purified by chromatography on silica gel with petroleum ether and petroleum ether/ethyl acetate. There were obtained 3.73 g (89.2%) of p-(4,4-ethylenedioxyl-1-butenyl)benzonitrile as a light yellowish oil.

b) A solution of 3.7 g of p-(4,4-ethylenedioxy-1-butenyl)benzonitrile in 50 ml of toluene was treated with 350 mg of palladium/carbon (5%) and the mixture was hydrogenated for 2.5 hours (hydrogen consumption 385 ml). The reaction mixture was then filtered (rinsing with diethyl ether) and the filtrate was evaporated. There were obtained 308 mg (82%) of p-(4,4-ethylenedioxybutyl)benzonitrile as a colourless, partially crystallizing oil.

c) A mixture of 2.8 g of p-(4,4-ethylenedioxybutyl)-benzonitrile, 56 ml of tetrahydrofuran and 56 ml of 10 percent hydrochloric acid was stirred for 3 hours at room temperature and then left to stand overnight. Thereafter, the reaction mixture was diluted with water and extracted three times with diethyl ether. The organic phases were washed twice with water, dried over magnesium sulphate, filtered and concentrated. There were obtained 2.6 g of 4-(p-cyanophenyl)butyraldehyde which was processed without additional purification.

d) A suspension of 6.5 g of methyl-triphenylphosphonium bromide in 50 ml of t-butyl methyl ether was treated with 2.1 g of potassium t-butylate at −5° C. and the mixture was then stirred at room temperature for 40 minutes. Subsequently, the mixture was treated at 0° C. with a solution of 2.6 g of 4-(p-cyanophenyl)butyraldehyde in 30 ml of t-butyl methyl ether and the resulting mixture was stirred for 1 hour at room temperature. Thereafter, the reaction mixture was treated with water and extracted three times with diethyl ether. The organic phases were washed twice with water, dried over magnesium sulphate, filtered and concentrated. The crystalline residue was dissolved in hot ethyl acetate, the solution was treated with petroleum ether and the precipitated triphenylphosphine was filtered off. The oil obtained after concentrating the filtrate was purified by chromatography on silica gel with ethyl acetate/petroleum ether (vol. 5:95), whereby 1.92 g of p-(4-pentenyl)benzonitrile were isolated as a light yellowish liquid.

e) A mixture of 1.9 g of p-(4-pentenyl)benzonitrile and a 10% solution of potassium hydroxide in diethylene glycol was boiled at 180° C. for 2 hours. The reaction mixture was then cooled to room temperature, adjusted to pH 3 with 23 percent hydrochloric acid, diluted with water and extracted four times with methylene chloride. The organic phases were washed twice with water, dried over magnesium sulphate, filtered and concentrated, whereby 2.12 g of p-(4-pentenyl)benzoic acid were isolated as brown crystals.

EXAMPLE 23 a) A solution of 3-butenylmagnesium bromide in diethyl ether (prepared from 172 mg of magnesium shavings and 0.604 ml of 4-bromo-1-butene in 10 ml of diethyl ether) was treated dropwise at room temperature with a solution of 1.0 g of p-[trans-4-(4-pentenyl)cyclohexyl]benzonitrile in 10 ml of toluene and the mixture was stirred for 17 hours at 45° C. Thereafter, the reaction mixture was treated cautiously at 0° C. with saturated ammonium chloride solution and partitioned three times in diethyl ether/water. The organic phases were washed twice with water, dried over magnesium sulphate, filtered and evaporated. Chromatographic separation of the yellow, crystalline residue (1.28 g) on silica gel with ethyl acetate/petroleum ether (vol. 3:97) gave 1.19 g (97%) of p-[trans-4-(4-pentenyl)cyclohexyl]-4-pentenoylphenone as a colourless oil.

b) A solution of 1.19 g of p-[trans-4-(4-pentenyl)cyclohexyl]-4-pentenoylphenone in 10 ml of ethanol and 10 ml of diethylene glycol was treated with 0.372 ml of hydrazine hydrate while gassing with argon and the mixture was then heated to reflux (bath temperature 110° C.) while stirring for 2 hours. Subsequently, the mixture was treated with 439 mg of solid potassium hydroxide, the bath temperature was raised to 210° C. and the ethanol was distilled off. After 2 hours at 210° C. the reaction was interrupted and the mixture was partitioned three times in water/petroleum ether. The organic extracts were washed twice with water, dried over magnesium sulphate and evaporated. Chromatographic separation of the residue (0.84 g) on silica gel with hexane as the eluent gave 0.725 g (64%) of 4-(4-pentenyl)-1-[trans-4-(4-pentenyl)cyclohexyl]benzene. Bulb-tube distillation gave, at 165° C./0.25 Torr, 530 mg of product as a colourless oil with m.p. −32.6° C.

The following compounds were prepared in an analogous manner:
4'-[trans-4-(1E-pentenyl)cyclohexyl]-4-(4-pentenyl)-biphenyl; m.p. 133.7° C.,
4'-[trans-4-(1E-pentenyl)cyclohexyl]-4-(4-pentenyl)-biphenyl; cl.p. (S-I) 182.5° C., not crystallizable.

EXAMPLE 24 a) A suspension of 91.0 g of pyridinium chlorochromate in 650 ml of methylene chloride was treated dropwise within 5 minutes while stirring at room temperature with a solution of 22.6 g of 5-hexen-1-ol in 70 ml of diethyl ether and the mixture was stirred for a further 2 hours. Subsequently, the mixture was treated with 400 ml of diethyl ether and stirred for a further 15 minutes. Thereafter, the reaction solution was decanted off from a separated black resin and filtered. Fractional distillation of the filtrate under normal pressure gave, at 110°-122° C., 11.88 g of 5-hexenal.

b) A suspension of 62.2 g of methoxymethyl-triphenylphosphonium chloride in 250 ml of diethyl ether was treated with 21.4 g of potassium t-butylate at 0° C. under nitrogen. The orange-red suspension obtained was treated dropwise within 15 minutes at 5°-10° C. with a solution of 11.88 g of 5-hexenal in 65 ml of diethyl ether and the mixture was stirred for a further 3 hours at room temperature. Thereafter, the reaction mixture was treated with 7.5 g of sodium hydrogen carbonate and 125 ml of water and stirred for 10 minutes. The aqueous phase was separated and back-extracted with 30 ml of diethyl ether. The organic phases were washed twice with 30 ml of water each time, dried over sodium sulphate and filtered. The filtrate was freed from solvent at 60° C. bath temperature under normal pressure. The distillation residue (a yellow liquid) was shaken with 400 ml of pentane until the undissolved residue had become solid. The suspension obtained was cooled to −25° C. and filtered. Fractional distillation of the filtrate under normal pressure gave, at 120°-143° C., 10.4 g of 1-methoxy-1,6-heptadiene.

c) 13.2 ml of trimethyl orthoformate were treated with 0.22 ml of boron trifluoride diethyl etherate at 3° C. under an inert gas atmosphere. The mixture was then treated dropwise within 5 minutes while stirring with 2.52 g of 1-methoxy-1,6-heptadiene. The reaction mixture was left to stand in an ice-bath for a further 3 hours, then treated with 0.22 ml of triethanolamine and concentrated in a rotary evaporator at 50° C. The residue was dissolved in 30 ml of hexane and the solution was washed with 5 ml of saturated sodium hydrogen carbonate solution and four times with 5 ml of water each time, dried over sodium sulphate and concentrated. Bulb-tube distillation of the residue (4.0 g) at 220° C./9 Torr gave 3.74 g of (4-pentenyl)malonaldehyde tetramethyl acetal as a colourless liquid.

d) A mixture of 3.74 g of (4-pentenyl)malonaldehyde tetramethyl acetal, 0.27 ml of water and 75 mg of acid monohydrate was heated for 2 hours at a bath temperature of 110° C. Thereafter, the mixture was treated with 0.12 ml of triethylamine, left to cool and poured into 80 ml of hexane. The reaction mixture was washed twice with 15 ml of saturated sodium hydrogen carbonate solution each time, dried over sodium sulphate and filtered. Concentration of the filtrate gave 2.4 g of crude 3-methoxy-2-(4-pentenyl)acrolein.

EXAMPLE 25

A solution of 21.2 g of 5-butyl-2-(p-isopropoxyphenyl)pyrimidine [prepared in accordance with synthesis variant 2 in J. prakt. Chem. 317, 617 (1975)] in 300 ml of methylene chloride was treated dropwise within 1 hour with a solution of 37 ml of titanium tetrachloride in 200 ml of methylene chloride while stirring at 0° C. The reaction mixture was stirred for a further 30 minutes at 0° C. and for 3 hours at room temperature and then poured on to 1 l of ice-water. The aqueous phase was extracted with 1.2 l of methylene chloride. The combined organic phases were washed neutral with water, dried over sodium sulphate, filtered and concentrated. The brown, solid crude product (15.0 g) was introduced, adsorbed on 75 g of silica gel, on to a column of silica gel in toluene/acetone (vol. 9:1) and eluted with the same solvent mixture. The product obtained (12.8 g) was boiled up with hexane, whereby 12.6 g of 5-butyl-2-(p-hydroxyphenyl)pyrimidine with m.p. 184.2°–184.6° C. were isolated.

EXAMPLE 26 a) 275 ml of a 1M solution of bromine in carbon tetrachloride were added dropwise while stirring at 10°–15° C. in the course of 5 hours to a colourless solution of 36.4 g of 3-butenylbenzene in 300 ml of carbon tetrachloride. The reaction mixture was left to stand overnight at room temperature and was then freed from solvent in vacuo. There were obtained 79.9 g of (3,4-dibromobutyl)benzene as a yellowish oil.

b) A nitrating solution (prepared by the dropwise addition of 16.5 g of 96 percent nitric acid to a stirred mixture of 8.2 ml of glacial acetic acid and 8.2 ml of acetic anhydride at 5°–9° C.) was added dropwise in the course of 50 minutes at 3°–4° C. to a solution, cooled to 0° C., of 40.0 g of (3,4-dibromobutyl)benzene in 48 ml of acetic anhydride. The yellowish solution was left to warm to room temperature over a period of 4 hours. After leaving to stand overnight the mixture was poured on to a mixture of 250 g of ice and 100 ml of water and treated with 13.5 g of sodium carbonate ($Na_2CO_3.10\ H_2O$). Extraction of the mixture with diethyl ether, washing the ethereal solutions with water, saturated sodium hydrogen carbonate solution and water, drying with sodium sulphate and concentration in vacuo gave 47.3 g of a brown oil containing 39.7% o-nitro derivative and 58.7% p-nitro derivative. Chromatography on silica gel in hexane and elution with hexane/toluene gave 14.2 g of 1-(3,4-dibromobutyl)-2-nitrobenzene, 13.7 g of isomer mixture and 18.2 g of 1-(3,4-dibromobutyl)-4-nitrobenzene.

c) A mixture of 52.1 g of sodium iodide, 300 ml of acetone and 28.6 g of 1-(3,4-dibromobutyl)-4-nitrobenzene was stirred under reflux for 3.5 hours. After cooling the brown suspension was freed from solvent in vacuo and the brown residue was taken up in diethyl ether and water. The separated iodine was reduced by adding solid sodium thiosulphate. The colourless ether solutions were washed with water, dried with sodium sulphate and concentrated in vacuo. The residue (14.9 g) was distilled in a high vacuum, whereby 13.4 g of 1-(3-butenyl)-4-nitrobenzene were obtained as an almost colourless liquid; b.p. 86°–89° C./0.2 Torr.

d) A solution of 11.9 g of 1-(3-butenyl)-4-nitrobenzene in 875 ml of methanol was treated with 6.5 g of magnesium shavings while stirring and gassing with nitrogen. After stirring for 4 hours the yellow, turbid reaction mixture was freed from methanol in vacuo. The residue was dissolved in 220 ml of water and 110 ml of 17 percent hydrochloric acid and the solution was extracted exhaustively with methylene chloride. The organic phases were washed neutral with water, dried over sodium sulphate and freed from solvent in vacuo. The residue (10.4 g) was treated with 100 ml of water and subjected to a steam distillation, 3.3 g of starting material could be recovered from the distillate by shaking out with methylene chloride. Extraction of the distillation residue with methylene chloride gave 7.0 g of a brown liquid which was dissolved in hexane and chromatographed on 260 g of silica gel in hexane. Hexane/toluene eluted 2.074 g of a mixture of starting material and 4,4'-di-(3-butenyl)azobenzene, then 0.353 g of mixed fractions and finally 4.358 g of crude azoxy compound as a dark yellow, liquid crystalline substance which later crystallized. Recrystallization from diethyl ether/methanol gave pure 4,4'-di-(3-butenyl)azoxybenzene with m.p. (C-N) 34.0° C., cl.p. (N-I) 75.5° C.

We claim:

1. A compound of the formula

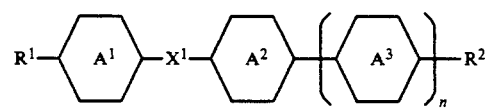

wherein n is the integer 0 or 1; rings $A^1$, $A^2$ and $A^3$ independently are 1,4-phenylene, 2-fluoro-1,4-phenylene or trans-1,4-cyclohexylene or one of these rings also is 2,5-disubstituted pyrimidine or trans-2,5-disubstituted m—dioxane; $X^1$ is a single covalent bond, —COO—, —OOC—, —$CH_2CH_2$—, p—$C_6H_4$—, —$CH_2CH_2$—p—$C_6H_4$—, —$CH_2CH_2$—p—$C_6H_4$—$CH_2CH_2$—or, when rings $A^1$ and $A^2$ are 1,4-phenylene, $X^1$ also can be —NON—; $R^2$ is 1E-alkenyl, 2Z-alkenyl, 3E-alkenyl, 4-alkenyl, (2E-alkenyl)oxy or (3alkenyl)oxy; $R^1$ is 1E-alkenyl, 2Z-alkenyl, 3E-alkenyl, 4-alkenyl or, when $R^2$ is alkenyloxy, $R^1$ also can be alkyl; and —NON— is —N=N(O)—or —N(O)=N—; with the proviso that the 1E-alkenyl or 2Z-alkenyl moiety is attached to other than an aromatic ring.

2. The compound of claim 1, wherein the rings $A^1$, $A^2$ and $A^3$ independently are 1,4-phenylene or trans-1,4-cyclohexylene or one of these rings also is 2,5-disubstituted pyrimidine or trans-2,5-disubstituted m-dioxane; $R^2$ is 1E-alkenyl, 2Z-alkenyl, 3E-alkenyl, 4-alkenyl, (2E-alkenyl)oxy or (3-alkenyl)oxy; and $R^1$ is 1E-alkenyl, 2Z-alkenyl, 3E-alkenyl, 4-alkenyl or, when $R^2$ is (2E-alkenyl)oxy or (3-alkenyl)oxy, $R_1$ also can be alkyl; with the proviso that the 1E-alkenyl or 2Z-alkenyl moiety is attached to other than an aromatic ring.

3. The compound of claim 1, wherein $R^1$ and $R^2$ are straight-chain residues defined in claim 1 having a maximum of 12 carbon atoms.

4. The compound of claim 3 wherein $R^1$ and $R^2$ have a maximum of 7 carbon atoms.

5. The compound of claim 1, wherein $R^2$ is (2E-alkenyl)oxy or one of $R^1$ and $R^2$ is 1E-alkenyl or 3E-alkenyl.

6. The compound of claim 1, wherein $X^1$ is a single covalent bond, —COO—, —OOC—, —$CH_2CH_2$— or p—$C_6H_4$—.

7. The compound of claim 1, wherein n is the integer 0.

8. The compound of claim 7, wherein n is the integer 0 and ring $A^2$ is 1,4-phenylene, trans-1,4-cyclohexylene or 2,4-disubstituted pyrimidine.

9. The compound of claim 8, wherein n is the integer 0, ring $A^1$ is trans-1,4-cyclohexylene, ring $A^2$ is 1,4-phenylene and $X^1$ is a single covalent bond, —COO—, —$CH_2CH_2$— or p—$C_6H_4$—.

10. The compound of claim 1, wherein ring $A^1$ is 2,5-disubstituted pyrimidine or trans-2,5-disubstituted m-dioxane, ring $A^2$ is 1,4-phenylene or trans-1,4-cyclohexylene and $X^1$ is a single covalent bond.

11. The compound of claim 1, wherein n is the integer 1 and ring $A^2$ is 1,4-phenylene or 2,5-disubstituted pyrimidine.

12. A liquid crystalline mixture with at least 2 components, wherein at least one of said components is a compound of formula

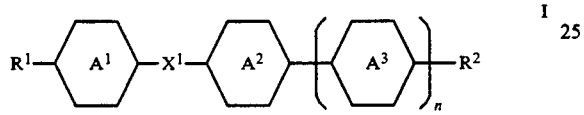

wherein n is the integer 0 or 1; rings $A^1$, $A^2$ and $A^3$ independently are 1,4-phenylene, 2-fluoro-1,4-phenylene or trans-1,4-cyclohexylene or one of these rings also is 2,5-disubstituted pyrimidine or trans-2,5-disubstituted m-dioxane; $X^1$ is a single covalent bond, —COO—, —OOC—, —$CH_2CH_2$—, p—$C_6H_4$—, —$CH_2CH_2$—p—$C_6H_4$—, —$CH_2CH_2$—p—$C_6H_4$—$CH_2CH_2$— or, when rings $A^1$ and $A^2$ are 1,4-phenylene, $X^1$ also can be —NON—; $R^2$ is 1E-alkenyl, 2Z-alkenyl, 3E-alkenyl, 4-alkenyl or alkenyloxy, with the proviso that the oxygen atom in alkenyloxy is linked with a saturated carbon atom; $R^1$ is 1E-alkenyl, 2Z-alkenyl, 3E-alkenyl, 4-alkenyl or, when $R^2$ is alkenyloxy, $R^1$ also can be alkyl; and —NON— is —N=N(O)—or —N(O)=N—; with the proviso that the 1E-alkenyl or 2Z-alkenyl moiety is attached to other than an aromatic ring.

13. An electro-optical cell comprising:
a) two plate means;
b) liquid crystal means disposed between the two plate means and including a compound of the formula

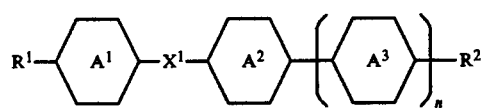

wherein n is the integer 0 or 1; rings $A^1$, $A^2$ and $A^3$ independently are 1,4-phenylene, 2-fluoro-1,4-phenylene or trans-1,4-cyclohexylene or one of these rings also is 2,5-disubstituted pyrimidine or trans-2,5-disubstituted m-dioxane; $X^1$ is a single covalent bond, —COO—, —OOC—, —$CH_2CH_2$—, p—$C_6H_4$—, —$CH_2CH_2$—p—$C_6H_4$—, —$CH_2CH_2$—p—$C_6H_4$—$CH_2CH_2$— or, when rings $A^1$ and $A^2$ are 1,4-phenylene, $X^1$ also can be —NON—; $R^2$ is 1E-alkenyl, 2Z-alkenyl, 3E-alkenyl, 4-alkenyl or alkenyloxy, with the proviso that the oxygen atom in alkenyloxy is linked with a saturated carbon atom; $R^1$ is 1E-alkenyl, 2Z-alkenyl, 3E-alkenyl, 4-alkenyl or, when $R^2$ is alkenyloxy, $R^1$ also can be alkyl; and —NON— is —N=N(O)—or —N(O)=N—; with the proviso that the 1E-alkenyl or 2Z-alkenyl moiety is attached to other than an aromatic ring;

c) means to apply an electric potential to the two plate means.

14. The compound of claim 1, wherein $R^2$ is (2E-alkenyl)oxy, or (3-alkenyl)oxy; and $R^1$ is alkyl.

* * * * *